US006586006B2

(12) United States Patent
Roser et al.

(10) Patent No.: US 6,586,006 B2
(45) Date of Patent: Jul. 1, 2003

(54) SOLID DELIVERY SYSTEMS FOR CONTROLLED RELEASE OF MOLECULES INCORPORATED THEREIN AND METHODS OF MAKING SAME

(75) Inventors: Bruce J. Roser, Cambridge (GB); Camilo Colaco, Cambridge (GB); Mohammed A. Z. Jerrow, Aberdeen (GB); Julian Blair, St. Ives (GB); Jaap Kampinga, Groningen (NL); James Lewis Wardell, Aberdeen (GB); John Alistair Duffy, Aberdeen (GB)

(73) Assignee: Elan Drug Delivery Limited, Nottingham (GB)

( * ) Notice: Subject to any disclaimer, the term of this patent is extended or adjusted under 35 U.S.C. 154(b) by 0 days.

(21) Appl. No.: 09/755,737

(22) Filed: Jan. 5, 2001

(65) Prior Publication Data

US 2001/0038858 A1 Nov. 8, 2001

Related U.S. Application Data

(63) Continuation of application No. 08/500,877, filed as application No. PCT/GB95/01861 on Aug. 4, 1995, now abandoned.

(30) Foreign Application Priority Data

Aug. 4, 1994 (GB) .............................................. 9415810

(51) Int. Cl.[7] .............................. A61K 9/14; A61K 9/70; A61K 9/50; A61K 47/00; A61F 2/00

(52) U.S. Cl. ...................... 424/484; 424/423; 424/443; 424/449; 424/426; 424/502; 514/777; 514/781

(58) Field of Search ................................. 514/777, 781, 514/23, 53; 424/484, 423, 443, 449, 426, 502

(56) References Cited

U.S. PATENT DOCUMENTS

| 979,993 A | 12/1910 | O'Byrne et al. |
|---|---|---|
| 3,557,717 A | 1/1971 | Chivers |
| 3,619,294 A | 11/1971 | Black et al. |
| 3,632,357 A | 1/1972 | Childs |

(List continued on next page.)

FOREIGN PATENT DOCUMENTS

| DE | 1 080 265 | 4/1960 |
|---|---|---|
| EP | 0 139 286 | 5/1985 |
| EP | 0 356 154 A2 | 2/1990 |

(List continued on next page.)

OTHER PUBLICATIONS

Hawley's Condensed Chemical Dictionary 12th Edition Von Nostrand Reinhold pp 938, 374, 16–17.
Levine et al. (1992) "Another view of trehalose for drying and stabilizing biological materials" *Biopharm* 5:36–40.
Skrabanja et al. (1994) "Lyophilization of Biotechnology Products" *PDA J. Pharm. Sci. Technol.* 48:311–317.

(List continued on next page.)

*Primary Examiner*—Thurman K. Page
*Assistant Examiner*—Blessing Fubara
(74) *Attorney, Agent, or Firm*—Morrison & Foerster LLP

(57) ABSTRACT

The present invention encompasses solid dose delivery systems for administration of guest substances. Preferred delivery systems are suitable for delivery of bioactive materials to subcutaneous and intradermal, intramuscular, intravenous tissue, the delivery system being sized and shaped for penetrating the epidermis. The delivery systems comprises a vitreous vehicle loaded with the guest substance and capable of releasing the guest substance in situ at various controlled rates. The present invention further includes methods of making and using the solid dose delivery systems.

47 Claims, 20 Drawing Sheets

U.S. PATENT DOCUMENTS

| | | | |
|---|---|---|---|
| 3,655,442 A | 4/1972 | Schwer et al. | |
| 3,745,682 A | 7/1973 | Waldeisen | |
| 3,948,263 A | 4/1976 | Drake, Jr. et al. | |
| 4,127,502 A | 11/1978 | Li Mutti et al. | |
| 4,158,544 A | 6/1979 | Louderback | |
| 4,244,949 A | 1/1981 | Gupta | |
| 4,326,524 A | 4/1982 | Drake, Jr. et al. | |
| 4,327,076 A | 4/1982 | Puglia et al. | |
| 4,327,077 A | 4/1982 | Puglia et al. | |
| 4,588,744 A | 5/1986 | McHugh | |
| 4,591,552 A | 5/1986 | Neurath | |
| 4,613,500 A | 9/1986 | Suzuki et al. | |
| 4,620,847 A | 11/1986 | Shishov et al. | |
| 4,680,027 A | 7/1987 | Parsons et al. | |
| 4,684,719 A | 8/1987 | Nishikawa et al. | |
| 4,701,417 A | 10/1987 | Portenhauser et al. | |
| 4,762,857 A | 8/1988 | Bollin, Jr. et al. | |
| 4,790,824 A | 12/1988 | Morrow et al. | |
| 4,793,997 A | 12/1988 | Drake et al. | |
| 4,812,444 A | 3/1989 | Mitsuhashi et al. | |
| 4,814,436 A | 3/1989 | Shibata et al. | |
| 4,824,938 A | 4/1989 | Koyama et al. | |
| 4,847,079 A | 7/1989 | Kwan | |
| 4,855,326 A * | 8/1989 | Fuisz | 514/777 |
| 4,861,627 A | 8/1989 | Mathiowitz et al. | |
| 4,865,871 A | 9/1989 | Livesey et al. | |
| 4,883,762 A | 11/1989 | Hoskins | |
| 4,891,319 A | 1/1990 | Roser | |
| 4,906,463 A | 3/1990 | Cleary et al. | |
| 4,997,856 A * | 3/1991 | Fuisz | 514/777 |
| 5,006,343 A | 4/1991 | Benson et al. | |
| 5,011,678 A | 4/1991 | Wang et al. | |
| 5,017,372 A | 5/1991 | Hastings | |
| 5,026,566 A | 6/1991 | Roser | |
| 5,049,389 A | 9/1991 | Radhakrishnan | |
| 5,075,291 A * | 12/1991 | DuRoss | 514/777 |
| 5,098,893 A | 3/1992 | Franks et al. | |
| 5,149,653 A | 9/1992 | Roser | |
| 5,204,108 A | 4/1993 | Illum | |
| 5,239,993 A | 8/1993 | Evans | |
| 5,240,843 A | 8/1993 | Gibson et al. | |
| 5,284,656 A | 2/1994 | Platz et al. | |
| 5,290,765 A | 3/1994 | Wettlaufer et al. | |
| 5,306,506 A | 4/1994 | Zema et al. | |
| 5,312,335 A | 5/1994 | McKinnon et al. | |
| 5,348,852 A | 9/1994 | Bonderman | |
| 5,354,934 A | 10/1994 | Pitt et al. | |
| 5,380,473 A | 1/1995 | Bogue et al. | |
| 5,387,431 A | 2/1995 | Fuisz | |
| 5,422,384 A | 6/1995 | Samuels et al. | |
| 5,425,951 A | 6/1995 | Goodrich, Jr. et al. | |
| 5,512,547 A | 4/1996 | Johnson et al. | |
| 5,567,439 A | 10/1996 | Myers et al. | |
| 5,589,167 A | 12/1996 | Cleland et al. | |
| 5,621,094 A | 4/1997 | Roser et al. | |

FOREIGN PATENT DOCUMENTS

| | | |
|---|---|---|
| EP | 0 383 569 A2 | 8/1990 |
| EP | 0 383 569 A3 | 11/1990 |
| EP | 0 415 567 | 3/1991 |
| EP | 0 433 679 | 6/1991 |
| EP | 0 357 665 | 3/1994 |
| EP | 0 383 569 B1 | 5/1994 |
| EP | 0 601 965 | 6/1994 |
| EP | 0 714 905 | 6/1996 |
| FR | 2238476 | 3/1975 |
| GB | 1381588 | 1/1975 |
| GB | 1533012 | 1/1978 |
| GB | 2206273 | 1/1989 |
| JP | 58-216695 | 12/1983 |
| JP | 63-502592 | 9/1988 |
| WO | WO 87/00196 | 1/1987 |
| WO | WO 87/05300 | 9/1987 |
| WO | WO 88/08298 | 11/1988 |
| WO | WO 89/06542 | 7/1989 |
| WO | WO 89/06976 | 8/1989 |
| WO | WO 90/05182 | 5/1990 |
| WO | WO 90/11756 | 10/1990 |
| WO | WO 91/16038 | 10/1991 |
| WO | WO 91/18091 | 11/1991 |
| WO | WO 92/02133 | 2/1992 |
| WO | WO 93/00951 | 1/1993 |
| WO | WO 93/02834 | 2/1993 |
| WO | WO 93/09832 | 5/1993 |
| WO | WO 93/10758 * | 6/1993 |
| WO | WO 93/11220 | 6/1993 |
| WO | WO 93/23110 | 11/1993 |
| WO | WO 94/07514 | 4/1994 |
| WO | WO 94/08552 | 4/1994 |
| WO | WO 94/13271 | 6/1994 |
| WO | WO 94/22423 | 10/1994 |
| WO | WO 94/24263 | 10/1994 |
| WO | WO 95/00127 | 1/1995 |
| WO | WO 95/06126 | 3/1995 |
| WO | WO 95/23613 | 9/1995 |
| WO | WO 95/24183 | 9/1995 |
| WO | WO 95/31479 | 11/1995 |
| WO | WO 95/33488 | 12/1995 |
| WO | WO 97/34689 | 9/1997 |
| WO | WO99/01463 * | 1/1999 |

OTHER PUBLICATIONS

Timko et al. (1984) "Thermal Analysis Studies of Glass Dispersion Systems" *Drug Devel. Ind. Pharm.* 10:425–451.

Akoh et al. (1987) "One stage synthesis of raffinose fatty acid polyesters" *J. Food Sci.* 52:1570–1576.

Blakeley et al., (1990) "Dry instant blood typing plate for bedside use" *Lancet* 336:854–855.

Colaco et al. (1992) "Extraordinary stability of enzymes dried in trehalose: Simplified molecular biology" *Bio/Tech.* 10:1007–1011.

Colaco et al., (1992) "Trehalose stabilization of biological molecules" *Biotechnol. Internat.* pp. 345–350.

Hahn et al., (1989) "Solid surfactant solutions of active ingredients in sugar esters" *Pharmaceutical research* 6:958–960.

Jovanovic–Peterson, L. et al. (1993). "Jet–injected insulin is associated with decreased antibody production and postprandial glucose variability when compared with needle–injected insulin in gestational diabetic women," *Diabetes Care* 16(11):1479–1484.

Khan (1984) "Chemistry and new uses of sucrose: How important?" *Pure & Appl. Chem.* 56:833–844.

Khan et al. (1990) "Cyclic acetals of 4,1',6'–trichloro–4,1',6'–trideoxy–galacto–sucrose and their conversion into methyl ether derivatives" *Carb. Res.* 198:275–283.

Khan et al. (1993) "Enzymic regioselective hydrolysis of peracetylated reducing disaccharides, specifically at the anomeric centre: Intermediates for the synthesis of oligosaccharides" *Tetra. Letts* 34:7767–7770.

Klein et al., (1987) "High velocity microprojectiles for delivering nucleic acids into living cells" *Nature* 327:70–73.

Lee, C. K. (1980). *Developments in Food Carbohydrate—2nd ed.* Applied Science Publishers, London (Table of Contents).

Pekarek et al. (1994) "Double–walled polymer microspheres for controlled drug release" *Nature* 367:258–260.

Roser (1991) "Trehalose drying: A novel replacement for freeze drying" *Biopharm* 4:47–53.

Roser (Jul. 1991) "Trehalose, a new approach to premium dried foods" *Trends in Food Sci. and Tech.* pp. 166–169.

Roser et al. (May 1993) "A sweeter way to fresher food" *New Scientist* pp. 25–28.

Sanchez et al., (1989) "Recombinant system for overexpression of cholera toxin B subunit in *Vibrio cholerae* as a basis for vaccine development" *Proc. Natl. Acad. Sci. USA* 86:481–485.

Takahashi et al., (1990) "Induction of CD8$^+$ cytotoxic T cells by immunization with purified HIV–1 envelope protein in ISCOMs" *Nature* 344:873–875.

Dialog® English Abstract of JP 58–216695 (Dec. 16, 1983).

Dialog® English Abstract of FR 2238476 (Mar. 28, 1975).

Dialog® English Abstract of JP 63–502592 (Sep. 29, 1988).

Letter from Bruce J. Roser to Raj Uppal (Aug. 14, 1997).

Letter from Kevin Appleton to Susan Lehnhardt, including index of art produced by Bruce J. Roser (Sep. 22, 1997).

Dialog® Search for references cited in letter from Bruce J. Roser to Raj Uppal (Aug. 14, 1997), 6 pages total.

Dialog® Search for Solidose Injection Devices, pp. 49–99 (Aug. 23, 1995).

Sakurai, Y. (ed) (1986) "Sogo Shokuhin Jiten" *Comprehensive Food Dictionary,* Sixth Edition, published by Dobun Shoin, Tokyo, Japan, pp. 203–204 (Dried Eggs), 208 (Dried Eggs, or Dehydrated Eggs), and 572 (Protein Denaturation), English translation provided pp. 1–9.

Summary of Reasons for Opposition to Japanese Patent Application No. 63–505533, pp. 1–5 (Mar. 15, 1994) with English translation.

Supplement of Reasons for Opposition of Japanese patent application No. 61–50394, pp. 1–23 (Jan., 1996) with English translation.

Grounds of Decision for Opposition of Japanese Patent Application No. 63–505533, pp. 1–6, (Jul., 1996) with English translation.

Kanna et al., (1974) "Denaturation of Fish Muscle Protein by Dehydration—V." *Bull Tokai Reg. Fish. Res. Lab.* 77:1–17.

Derwent® WPI File 351, English Abstract of PCT publication No. WO 87/05300 (Sep. 11, 1987).

Derwent® WPI File 351, English Abstract of Japanese publication No. 8298125 (Jun. 7, 1982).

Decision on Opposition, Kokoku 5–81232, corresponding to U.S. patent application Serial No. 5,026,566, 6 pages total.

Opposition Brief for Japanese patent application No. 63–505533 (English translation included), 17 pages total. (See Supplement of Reasons for Opposition in Japanese).

Toyama, A. (ed), (1986) *Handbook of Natural Product for food processing,* 9th Edition, Osaka, Japan, Shokuhin to Kagaku Sha, pp. 384 and 495 (ISBN4–87994–048–8).

Encyclopaedia Chimica, panel of Kagaku–Daijiten, Ed., vol. 7, pp. 310, 311 and English translation (1964).

Decision on Opposition for Japanese patent application No. 63–505533, filed on Apr. 12, 1996 (English translation included).

Japanese document regarding Opposition to Japanese patent application No. 63–505533 (English translation included), Abridged translation of specification for PCT patent publication No. WO 87/00196, one page total.

Advertisement for "Stop'n Grow" Manufactured by The Mentholatum Co. Ltd., East Kilbride, Scotland G74 SPE.

Facsimile from Dr. D. L. Smith to Dr. B. Roser regarding product information of Stop'n Grow, (Jun. 26, 1997), 7 pages.

Letter from David T. Welsh (University of Dundee) to Dr. A. Tunnacliffe (Quadrant Research Foundation) dated Nov. 16, 1995, one page total.

*Development of a dry and thermostable oral polio vaccine,* Progress Report QHCL, RIVM and RUG, May 1993–Oct. 1993, (Apr. 22, 1994), 9 pages total.

*Development of a dry and thermostable oral polio vaccine,* Progress Report QHCL and RIVM Nov. 1993–Apr. 1994, (Apr. 22, 1994), 11 pages total.

*Stability and characterization of protein and peptide drugs,* Wang et al. (eds.), 1993, Table of contents enclosed herewith.

Chiou et al., (Sep. 1971) "Pharmaceutical applications of solid dispersion systems" *J. Pharm.* 60(9):1281–1302.

Vain et al., (1993) "Development of the particle inflow gun" *Plant Cell, Tissue and Organ Culture* 33:237–246.

* cited by examiner

SOLID DELIVERY SYSTEMS FOR CONTROLLED RELEASE OF MOLECULES INCORPORATED THEREIN AND METHODS OF MAKING SAME

CROSS REFERENCE TO RELATED APPLICATIONS

This application is a continuation of U.S. Ser. No. 08/500,877, filed Aug. 18, 1997, now abandoned which is a 371 of PCT/GB95/01861, filed Aug. 4, 1995, which claims priority to United Kingdom application no. 9415810, filed Aug. 4, 1994 and to U.S. Ser. No. 08/349,029, filed Dec. 2, 1994, the disclosures of each of which are incorporated herein by reference in their entirety.

FIELD OF THE INVENTION

The present invention relates generally to solid delivery systems for storage, distribution and controlled delivery of molecules and, more specifically, to solid dose delivery systems comprising a vitreous vehicle and guest substances. Methods of making the delivery systems and methods of use thereof are also provided.

BACKGROUND OF THE INVENTION

Solid delivery systems are useful in a wide variety of applications such as controlled release of labile molecules, particularly bioactive materials such as pharmaceutical agents, enzymes, vaccines and biological control agents such as fertilisers, pesticides and pheromones.

Solid dose delivery of bioactive materials to biological tissues such as mucosal, dermal, ocular, subcutaneous, intradermal and pulmonary offers several advantages over previous methods such as topical applications of liquids, transdermal administration via so-called "patches" and hypodermic injection. Solid dose delivery can be by direct transdermal delivery of the solid dose which reduces the risk of infection by eliminating the use of conventional needles and syringes and provides for more accurate dosing than multidose vials, and minimizes or eliminates the discomfort which often attends hypodermic injection. Several solid dose delivery systems have been developed including those utilizing transdermal and ballistic delivery devices.

Topical delivery is utilized for a variety of bioactive materials such as antibiotics for wound healing. These topical ointments, gels, creams, etc. must be frequently reapplied in order to remain effective. This is particularly difficult in the case of burn wounds and ulcers.

Devices used for administering drugs transdermally usually comprise laminated composites with a reservoir layer of drug with the composite being adhered to the skin, i.e., transdermal patch, such as described in U.S. Pat. No. 4,906,463. However, many drugs are not suitable for transdermal delivery, nor have transdermal drug release rates for those capable of such delivery been perfected.

Subdermal implantable therapeutic systems have also been formulated for slow release of certain pharmaceutical agents for extended periods of time such as months or years. A well-known example is the Norplant® for delivery of steroid hormones.

In membrane permeation-type controlled drug delivery, the drug is encapsulated within a compartment that is enclosed by a rate-limiting polymeric membrane. The drug reservoir may contain either drug particles or a dispersion (or solution) of solid drug in a liquid or a matrix type dispersing medium. The polymeric membrane may be fabricated from a homogeneous or a heterogeneous nonporous polymeric material or a microporous or semipermeable membrane. The encapsulation of the drug reservoir inside the polymeric membrane may be accomplished by molding, encapsulation, microencapsulation, or other techniques. The implants release drugs by dissolution of the drug in the inner core and slow diffusion across the outer matrix. The drug release from this type of implantable therapeutic system should be relatively constant and is largely dependent on the dissolution rate of the drug in the polymeric membrane or the diffusion rate across or a microporous or semipermeable membrane. The inner core may substantially dissolve over time; however, in devices currently in use, the outer matrix does not dissolve.

Implants are placed subcutaneously by making an incision in the skin and forcing the implants between the skin and the muscle. At the end of their use, if not dissolved, these implants are surgically removed. U.S. Pat. No. 4,244,949 describes an implant which has an outer matrix of an inert plastic such as polytetrafluoroethylene resin. Examples of this type of implantable therapeutic system are Progestasert IUD and Ocusert system.

Other implantable therapeutic systems involve matrix diffusion-type controlled drug delivery. The drug reservoir is formed by the homogeneous dispersion of drug particles throughout a lipophilic or hydrophilic polymer matrix. The dispersion of drug particles in the polymer matrix may be accomplished by blending the drug with a viscous liquid polymer or a semisolid polymer at room temperature, followed by cross-linking of the polymer, or by mixing the drug particles with a melted polymer at an elevated temperature. It can also be fabricated by dissolving the drug particles and/or the polymer in an organic solvent followed by mixing and evaporation of the solvent in a mold at an elevated temperature or under vacuum. The rate of drug release from this type of delivery device is not constant. Examples of this type of implantable therapeutic system are the contraceptive vaginal ring and Compudose implant. PCT/GB 90/00497 describes slow release glassy systems for formation of implantable devices. The described implants are bioabsorbable and need not be surgically removed. However, insertion is by surgical means. Moreover, these devices are severely limited in the type of bioactive material that can be incorporated as these have to be stable to heat and/or solvent to enable incorporation into the delivery device.

In microreservoir dissolution-controlled drug delivery, the drug reservoir, which is a suspension of drug particles in an aqueous solution of a water-miscible polymer, forms a homogeneous dispersion of a multitude of discrete, unleachable, microscopic drug reservoirs in a polymer matrix. The microdispersion may be generated by using a high-energy-dispersing technique. Release of the drug from this type of drug delivery device follows either an interfacial partition or a matrix diffusion-controlled process. An example of this type of drug delivery device is the Syncro-Mate-C Implant.

In the case of cast polymeric implants, bioactive materials that cannot withstand organic solvents are not suitable for use. In the case of extruded polymer systems, bioactive materials that cannot withstand the elevated temperatures necessary to form the implants are unsuitable for use. In all cases, bioactive materials that are unstable at body temperature, particularly over long time periods, are unsuitable for use.

A variety of formulations have been provided for administration in aerosolized form to mucosal surfaces, particularly "by-inhalation" (naso-pharyngeal and pulmonary). Compositions for by-inhalation pharmaceutical administration generally comprise a liquid formulation of the pharmaceutical agent and a device for delivering the liquid in aerosolized form. U.S. Pat. No. 5,011,678 describes suitable compositions containing a pharmaceutically active substance, a biocompatible amphiphilic steroid and a biocompatible (hydro/fluoro) carbon propellant. U.S. Pat. No. 5,006,343 describes suitable compositions containing liposomes, pharmaceutically active substances and an amount of alveolar surfactant protein effective to enhance transport of the liposomes across a pulmonary surface.

One drawback to the use of aerosolized formulations is that maintenance of pharmaceutical agents in aqueous suspensions or solutions can lead to aggregation and loss of activity and bioavailability. The loss of activity can be partially prevented by refrigeration; however, this limits the utility of these formulations. This is particularly true in the case of peptides and hormones. For instance, synthetic gonadotropin releasing hormone (GnRH) analogs, such as the agonist nafarelin or the antagonist ganirelex, are designed for high potency, increased hydrophobicity and membrane binding. The compounds have sufficient hydrophobic character to aggregate in aqueous solution and to form an ordered structure that increases in viscosity with time. Thus bioavailability in nasal or pulmonary formulations may be prohibitively low. The use of powdered formulations overcomes many of these drawbacks. The requisite particle size of such powders is 0.5–5 microns in order to attain deep alveolar deposition in pulmonary delivery. Unfortunately, powders of such particle size tend to absorb water and clump, thus diminishing deposition of the powder in the deep alveolar spaces. Although powders with larger particle size are suitable for delivery to the naso-pharynx region, the tendency of powders to clump decreases the available particle surface area for contact with, and absorption through, these membranes. Devices which disaggregate clumps formed by electrostatic interactions are currently in use (e.g., the Turbohaler™); however, these do not disaggregate moisture-induced clumps. It would be advantageous to have powders which do not absorb moisture and clump, thus increasing the effective pulmonary concentration of the drug.

Solid dose delivery vehicles for ballistic, transdermal administration have also been developed. For example, in U.S. Pat. No. 3,948,263, a ballistic animal implant comprised of an exterior polymeric shell encasing a bioactive material is described for veterinary uses. Similarly, in U.S. Pat. No. 4,326,524, a solid dose ballistic projectile comprising bioactive material and inert binder without an exterior casing is disclosed. Delivery is by compressed gas or explosion. Gelatin covered tranquilizing substances carried by ballistic projectiles for implant are also described in U.S. Pat. No. 979,993. These ballistic devices, however, are suited solely to large animal veterinary applications due to the relatively large size of the dose delivered, typically on the order of millimeters.

Ballistic delivery at the cellular level has also been successful. The general principle of ballistic administration is the use of a supersonic wavefront, created by the release of compressed gas, to propel the particles contained in an adjoining chamber. For example, nucleic acids adsorbed on tungsten microprojectile particles have been successfully delivered to living epidermal plant cells. See, Klein (1987) *Nature* 327:70–73. A better controlled device is the particle inflow gun (PIG). Vain et al. (1993) *Plant Cell, Tissue and Organ Culture* 33:237–246.

Devices have been described which fire ampules containing medication using gas pressure. U.S. Pat. No. 4,790,824; and PCT/GB 94/00753. Several devices that inject fluids have also been described. U.S. Pat. Nos. 5,312,335 and 4,680,027. There are few existing formulations suitable for ballistic delivery, however. Powder formulations of pharmaceuticals in their present form are unsuitable for ballistic administration. Particles of available powder forms are generally irregular, varying in size, shape and density. This lack of uniformity leads to powder deposit and loss at the skin surface during administration, as well as problems in control and consistency of the depth of delivery to subcutaneous and intradermal tissues.

Thus, for ballistic delivery, it would be advantageous to provide solid drug delivery systems of defined size, shape, density and dissolution rate, to ensure more uniform distribution. Additional benefits would accrue if the shape of the vehicle could be controlled to facilitate or control penetration of the epidermis and hard layers of the skin. Small delivery system size, preferably coupled with high momentum delivery, would also increase the comfort of administration and minimize tissue damage. The manufacture of such a solid dose delivery system should be such that neither the delivery vehicle nor the guest substance being delivered is damaged nor its efficacy decreased. Furthermore, the guest substance should remain stable when loaded within or on the vehicle so that efficacious administration can be achieved, and storage of the loaded delivery system is facilitated. Manufacture of the solid dose delivery vehicle and its loading with guest material to obtain a solid dose delivery system and the administration of the system should also be relatively simple and economical.

All references cited herein are hereby incorporated by reference.

SUMMARY OF THE INVENTION

The present invention encompasses solid, glassy, delivery vehicles suitable for loading with a wide variety of substances or "guests" to obtain solid delivery systems. The choice of glassy delivery vehicles is determined by the nature of the guest substances and desired delivery rate of the guest substance. A wide variety of delivery rates and types are provided. Preferred guest substances, buffers, adjuvants and additional stabilizers are also provided. The delivery systems can be sized and shaped for a variety of modes of administration.

The invention comprises rapidly soluble solid dose delivery systems comprising a stabilizing polyol (SP) and a guest substance. These delivery systems can be formulated into powders of homogeneous particle size and larger, implantable forms.

The invention further encompasses novel glassy vehicles formed from hydrophobically-derivatized carbohydrates (HDCs). These HDCs are non-toxic and the release of guests from these systems is highly controllable for the release of guests over extended time periods. The release from HDC delivery systems can be effected by devitrification, dissolution and/or hydrolysis. The HDC delivery systems are uniquely suited to delivery of hydrophobic guest substances such as pesticides, pheromones, steroid hormones, peptides, peptide mimetics, antibiotics and other organic pharmaceuticals such as synthetic corticosteroids, bronchodilators and immunomodulators and immunosuppressants like cyclosporin A (CSA).

The invention further encompasses coformulations of the different glassy vehicles to provide novel combination delivery systems. The combination delivery systems comprise HDCs combined with SPs and/or other slowly water soluble glassy materials, such as carboxylate, nitrate and phosphate glasses, to produce solid dose delivery systems with a wide variety of novel properties.

The invention encompasses solid dose delivery systems for multiphasic delivery comprising an outer portion comprising an HDC, slowly soluble in aqueous solution having a hollow compartment therein, and an inner portion residing in the compartment, the inner portion comprising at least one SP and a therapeutically effective amount of at least one guest substance.

The invention also encompasses methods of delivering bioactive materials by providing the solid dose delivery systems described above and administering the system to a biological tissue. Administration can be mucosal, oral, topical, subcutaneous, intradermal, intramuscular, intravenous and by-inhalation.

The invention further encompasses methods of making the solid dose delivery systems. The SP and/or HDC, guest substances and any other components are mixed and processed by a wide variety of methods, including dissolving in the melt and subsequent quenching, spray drying, freeze drying, air drying, vacuum drying, fluidized-bed drying, co-precipitation and super-critical fluid evaporation. The resulting glass can be heated to soften and can then be extruded, drawn or spun into solid or hollow fibers. The dried components can also be mixed in aqueous or organic solutions and dried, such as by spray drying, freeze drying, air drying, vacuum drying, fluidized-bed drying, co-precipitation and super-critical fluid evaporation.

The invention further provides methods of making delivery systems suitable for slow or pulsatile release of guest substances. The methods include combining guest substances in solid solutions of stabilizing glass-forming polyols and/or HDCs and/or other glass formers with dissolution or degradation rates slower than that of the SP, and processing the components as described above. The ratio of materials can be controlled so as to provide a wide range of precisely defined release rates. The coformulations of SP and/or HDCs and other water-soluble and/or biodegradable glasses, plastics and glass modifiers produced thereby are also encompassed by the present invention.

The solid dose systems and methods of the invention also encompass solid dose forms which comprise fibers, spheres, tablets, discs, particles and needles of relatively homogeneous size distribution. The vehicles can be either microscopic or macroscopic.

A wide variety of guest substances are suitable for use in accord with the present invention, including, but not limited to, diagnostic, therapeutic, prophylactic and other active agents. The delivery systems and methods of use thereof provide for a variety of dosing schemes for delivery of the guest substances and are suitable for a wide range of uses including agricultural, veterinary and human applications.

BRIEF DESCRIPTION OF THE DRAWINGS

FIG. 1 is described in Example 2.

FIG. 14 is described in Example 9.

FIG. 15 is described in Example 9.

FIG. 16 is described on Example 10.

FIG. 17 is described in Example 10.

FIG. 18 is described in Example 10.

DETAILED DESCRIPTION OF THE INVENTION

Figure 1:
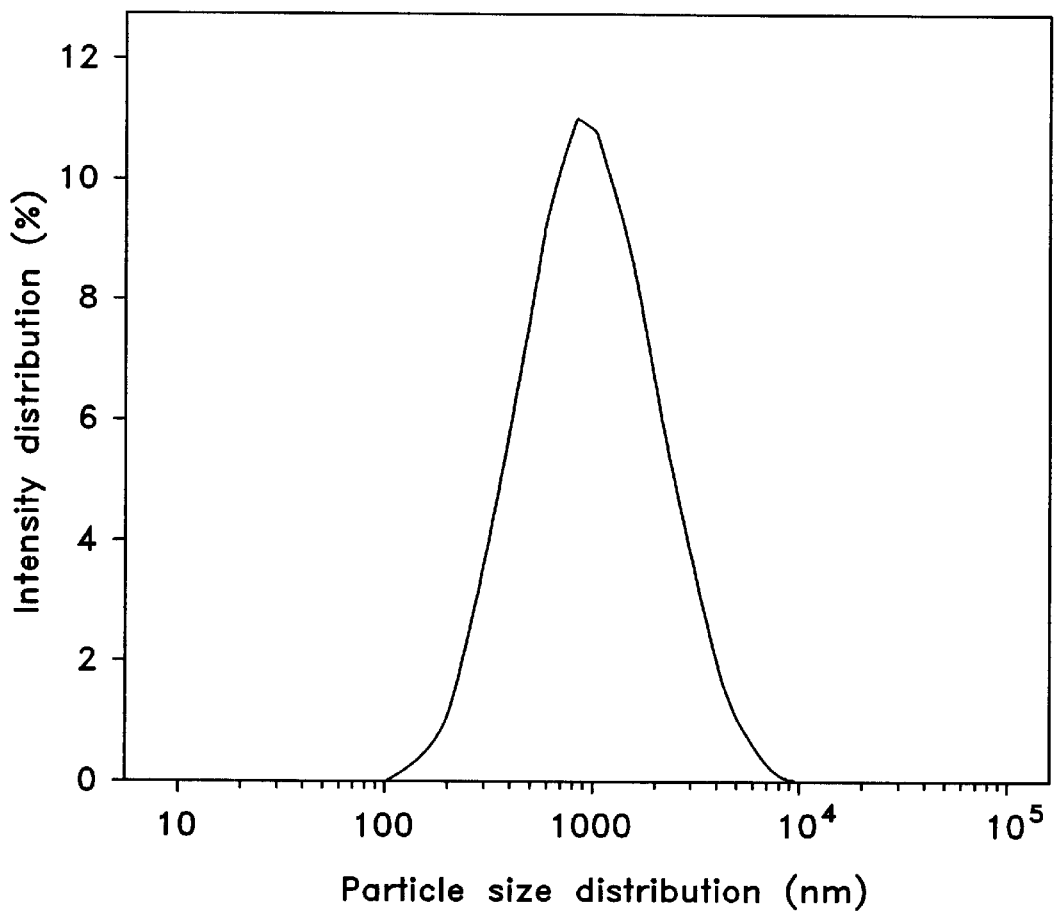
FIG. 1 is a graph depicting typical particle size distribution of micronized trehalose glass powder suitable for administration by inhalation.

The present invention comprises solid dose delivery systems comprising solid dose delivery vehicles and guest substances. The delivery systems are formulated to provide precise delivery rates of the guest substances incorporated therein. The delivery systems are particularly suitable for delivery of bioactive molecules to animals including humans.

Also encompassed by the invention are methods of delivery of therapeutic agents including, but not limited to, mucosal, oral, topical, subcutaneous and intradermal, intramuscular, intravenous and by-inhalation administration.

The invention also encompasses methods of making the delivery systems.

"Solid dose" as used herein, means that a guest substance incorporated in the vehicle is in solid rather than liquid form and the solid form is the form used for delivery. Guest substances are those molecules, macromolecules and macromolecular assemblies, synthetic and natural, and cellular fractions, live and dead cells, bacteria and viruses and other actives incorporated into the vehicle; a wide variety of guest substances are suitable for use herein and are described below. By "effective amount" of guest substance, is meant an amount to achieve the affect desired. For instance, with a bioactive material, an effective amount is one which effects the desired physiological reaction. The vehicle is in solid form and is amorphous or glassy in nature. Other additives, buffers, dyes etc. may be incorporated into the delivery systems. As used herein, the term "vehicle" includes all the glass-forming substances embodied in the claimed invention. The term "delivery system(s)" includes the solid dose forms comprising the vehicles and guest substances. Delivery systems formed from specific vehicles are given distinct names as indicated, unless otherwise indicated, the term delivery system encompasses each of these.

In one embodiment, the invention relates to solid dose systems with rapid release rates of the guest substances. In this embodiment, the vehicle is a SP. It has now been found that SPs can be processed to obtain powders with homogeneous distribution of particle sizes in the form of either microspheres or needles. The SPs can also be processed to form macroscopic delivery forms suitable for formulation of implantable devices. A wide variety of dose forms and methods of making the dose forms are described herein. These SPs have been found to be particularly useful where otherwise denaturing conditions would render impossible the formulation of solid dosage forms of bioactive materials. In particular, such conditions include elevated temperatures (those above which the bioactive material is otherwise denatured) and the presence of organic solvents.

In another embodiment, the invention relates to solid dose systems with novel defined and controllable release rates of the guest substances. In this embodiment, the vehicle is an organic carboxylate glass. It has now been found that organic carboxylates form stable amorphous vehicles by solvent evaporation. These organic glasses release incorporated guest substances at precisely defined rates depending on the composite carboxylate anion and metal cation used. Like the vehicles comprising SPs, these glasses can be processed, either singly or in mixtures with other organic carboxylates and/or SPs and/or HDCs, to obtain powders with homogeneous particle size distribution, in the form of microspheres, needles and/or implantable devices to form a wide variety of macroscopic delivery forms.

In a further embodiment, the invention relates to solid dose systems with novel defined and controllable release rates of the guest substances. In this embodiment, the vehicle is a hydrophobic carbohydrate derivative (HDC). It has now been found that HDCs form stable glassy vehicles that release guest substances under aqueous conditions at precisely defined rates depending on the carbohydrate, the hydrophobic moiety(ies) used to derivatize the carbohydrate and the degree of derivatization. Like the vehicles comprising SPs, those comprising HDCs can be processed to obtain powders with homogeneous distribution of particle sizes in the form of either microspheres and needles. The HDCs can also be processed to form a wide variety of macroscopic delivery forms.

The dose forms and methods of making the dose forms are described herein. These delivery systems have been found to be particularly useful where the nature of the guest substance would render impossible the formulation of solid dosage forms as they provide delivery systems for hydrophobic guest substances which are either difficult to formulate into dosage forms or to obtain effective physiologic concentrations of due to insolubility in aqueous solvents.

The delivery systems exist as solid solutions, emulsions, suspensions or coacervates of the guest substance in the solid vehicle. The guest substance is resistant to higher temperatures within the vehicle than alone. The exact temperature resistance depends on the vehicle used. Thus, the components of the delivery systems can be maintained as melts for brief periods without damaging the guest substances during processing. In the same way, the delivery systems can be further processed and are resistant to damage during sintering with nitrate and/or carboxylate and/or HDCs and/or other glass-forming substances.

The invention further encompasses coformulations of various delivery vehicles and systems to provide a wide variety of combination delivery vehicles.

The present invention encompasses compositions and methods of making the compositions. Although singular forms may be used, more than one vehicle, more than one guest substance and more than one additive may be present. Determination of the effective amounts of these compounds is within the skill of one in the art.

Stabilizing Polyol Delivery Systems

The invention encompasses solid dose delivery systems in which the delivery vehicle comprises a stabilizing polyol. These are termed "SP delivery systems". It has now been found that the SP delivery systems can be processed to a wide variety of solid dose forms particularly suited to therapeutic administration of guest substances.

SPs include, but are not limited to, carbohydrates. As used herein, the term "carbohydrates" includes, but is not limited to, monosaccharides, disaccharides, trisaccharides, oligosaccharides and their corresponding sugar alcohols, polysaccharides and chemically modified carbohydrates such as hydroxyethyl starch and sugar copolymers (Ficoll). Both natural and synthetic carbohydrates are suitable for use herein. Synthetic carbohydrates include, but are not limited to, those which have the glycosidic bond replaced by a thiol or carbon bond. Both D and L forms of the carbohydrates may be used. The carbohydrate may be non-reducing or reducing. Suitable vehicles are those in which a guest substance can be dried and stored without losses in significant activity by denaturation, aggregation or other mechanisms. Prevention of losses of activity can be enhanced by the addition of various additives such as inhibitors of the Maillard reaction as described below. Addition of such inhibitors is particularly preferred in conjunction with reducing carbohydrates.

Reducing carbohydrates suitable for use in the present invention are those known in the art and include, but are not limited to, glucose, maltose, lactose, fructose, galactose, mannose, maltulose, iso-maltulose and lactulose.

Non-reducing carbohydrates include, but are not limited to, trehalose, raffinose, stachyose, sucrose and dextran. Other useful carbohydrates include non-reducing glycosides of polyhydroxy compounds selected from sugar alcohols and other straight chain polyalcohols. The sugar alcohol glycosides are preferably monoglycosides, in particular the compounds obtained by reduction of disaccharides such as lactose, maltose, lactulose and maltulose. The glycosidic group is preferably a glucoside or a galactoside and the sugar alcohol is preferably sorbitol (glucitol). Particularly preferred carbohydrates are maltitol (4-O-β-D-glucopyranosyl-D-glucitol), lactitol (4-O-β-D-galactopyranosyl-D-glucitol), palatinit (a mixture of GPS, α-D-glucopyranosyl-1→6-sorbitol and GPM, α-D-glucopyranosyl-1→6-mannitol), and its individual sugar alcohols, components GPS and GPM.

Preferably, the SP is a carbohydrate that exists as a hydrate, including trehalose, lactitol and palatinit. Most preferably, the SP is trehalose. It has now been found that, surprisingly, solid dose delivery systems containing certain sugar hydrates like trehalose lack the "stickiness" or "tackiness" of solid dose forms containing other carbohydrates. Thus, for manufacture, packaging and administration, trehalose is the preferred SP.

Trehalose, (α-D-glucopyranosyl-α-D-glucopyranoside), is a naturally occurring, non-reducing disaccharide which was initially found to be associated with the prevention of desiccation damage in certain plants and animals which can dry out without damage and can revive when rehydrated. Trehalose has been shown to be useful in preventing denaturation of proteins, viruses and foodstuffs during desiccation. See U.S. Pat. Nos. 4,891,319; 5,149,653; 5,026,566; Blakeley et al. (1990) *Lancet* 336:854–855; Roser (July 1991) *Trends in Food Sci. and Tech.* 166–169; Colaco et al. (1992) *Biotechnol. Internat.*, 345–350; Roser (1991) *BioPharm.* 4:47–53; Colaco et al. (1992) *Bio/Tech.* 10:1007–1011; and Roser et al. (May 1993) *New Scientist*, pp. 25–28.

Other SPs suitable for use herein are described for instance in, WO 91/18091, 87/00196 and U.S. Pat. Nos. 4,891,319 and 5,098,893 which describe the use of polyols as glasses for stabilizing molecules during drying and storage for reconstitution before use. The solid dosage forms encompassed by the present invention have now been found to be suitable for use directly, as delivery systems for controlled release of incorporated guest substances. Additionally, these polyols can be used in combination with other amorphous matrices to yield delivery systems which have now been found to have a wide range or release rates and characteristics which are readily and accurately controllable to produce unique solid dose systems.

It has also now been found that guest substances preferentially soluble in organic solvents can be dried in trehalose from an organic/aqueous solvent mixture to give a conformulation that is now readily reconstituted in aqueous solvents. The present invention encompasses solid dose systems obtained in this manner. Methods of making the dried material and compositions obtained thereby are provided by the invention. The guest substance is dissolved in an organic/aqueous solvent in combination with an effective amount of trehalose and then dried. This gives a solid solution, emulsion, suspension or coacervate of the guest substance in a trehalose glass which then readily dissolves in an aqueous solution to give a finely dispersed suspension of the insoluble guest substance. It has now been shown that the immunosuppressant CSA (which is poorly soluble in water and normally administered as an oil emulsion) in a solution of trehalose in a 1:1 ethanol:water mixture can be dried to give a clear glass of trehalose containing CSA. This glass can be milled to give a free flowing powder, which can also be tabletted, which when added to water dissolves instantaneously to give a finely dispersed suspension of CSA in water.

HDC Delivery Systems

The invention further encompasses solid dose delivery systems in which the vehicle contains at least one HDC. These are termed "HDC delivery systems". HDCs form a separate group of non-toxic carbohydrate derivatives suitable for use in forming the solid dose vehicle. Although many HDCs have been synthesized, the advantages of their facile glass formation has not previously been reported. The invention thus encompasses the glassy form of these HDCs which is also referred to as an amorphous matrix-forming composition. The HDC delivery systems are particularly suited for use in controlled, pulsatile or delayed release of guest substances. Any of the guest substances described herein may be incorporated in the HDC delivery systems.

As shown herein, HDCs readily form glasses either from a quenched melt or from an evaporated organic solvent. The HDCs can also be processed by the methods described for the SPs.

As used herein, HDC refers to a wide variety of hydrophobically derivatized carbohydrates where at least one hydroxyl group is substituted with a hydrophobic moiety including, but not limited to, esters and ethers. Numerous examples of suitable HDCs and their syntheses are described in Developments in Food Carbohydrate—2 ed. C. K. Lee, Applied Science Publishers, London (1980). Other syntheses are described for instance, in Akoh et al. (1987) *J. Food Sci.* 52:1570; Khan et al. (1993) *Tetra. Letts* 34:7767; Khan (1984) *Pure & Alpl. Chem.* 56:833–844; and Khan et al. (1990) *Carb. Res.* 198:275–283. Specific examples of HDCs include, but are not limited to, sorbitol hexaacetate (SHAC), α-glucose pentaacetate (α-GPAC), β-glucose pentaacetate (β-GPAC), 1-0-Octyl-β-D-glucose tetraacetate (OGTA), trehalose octaacetate (TOAC), trehalose octapropanoate (TOPR), sucrose octaacetate (SOAC), cellobiose octaacetate (COAC), raffinose undecaacetate (RUDA), sucrose octapropanoate, cellobiose octapropanoate, raffinose undecapropanoate, tetra-O-methyl trehalose and di-O-methyl-hexa-O-acetyl sucrose. An example of a suitable HDC where the carbohydrate is trehalose is:

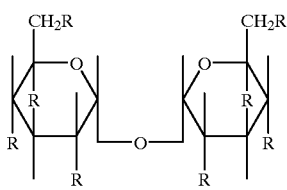

formula 1

In formula 1, R represents a hydroxyl group, or less hydrophilic derivative thereof, such as an ester or ether or any functional modifications thereof where at least one R is not hydroxyl but a hydrophobic derivative. Suitable functional modifications include, but are not limited to, where the oxygen atom is replaced by a heteroatom, such as N or S. The degree of substitution can also vary, and may be a mixture of distinct derivatives. Full substitution of the hydroxyl groups need not occur and provides an option to alter physical properties (such as solubility) of the vehicle. R can be of any chain length from $C_2$ upwards and may be straight, branched, cyclic or modified. While formula 1 depicts the disaccharide trehalose, any of the carbohydrates discussed herein may be the carbohydrate backbone and the position of the glycosidic linkage and saccharide chain length can vary. Typically, the practical range in terms of cost and efficiency of synthesis is a pentasaccharide; however, the invention is not limited to saccharides of any particular type, glycosidic linkage or chain length. Various other aspects of the HDCs are not limiting. For instance, the component saccharides of each HDC can also be varied, the position and nature of the glycosidic bonding between the saccharides may be altered and the type of substitution can vary within an HDC. A representative example of a HDC with mixed substitution with esters and ethers is 1-o-Octyl-β-D-glucopyranoside 2,3,4,5-tetraacetate:

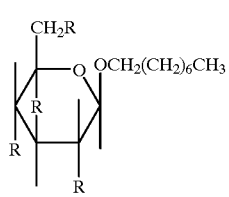

formula 2

Where R is $O_2CCH_3$.

The ability to modify the properties of HDCs by slight alterations in composition renders them uniquely suited to solid dose vehicles, particularly compared to polymeric systems which often depend on regions of crystallinity to vary their properties, particularly bioerosion. The HDC delivery systems can be tailored to have precise properties such as release rates of guest substances. Such tailoring can be by varying the modifications of a particular carbohydrate or by combining a variety of different HDCs.

Pure single HDC glasses have been found to be stable at ambient temperatures and up to at least 60% humidity. Mixtures of HDC glasses incorporating certain guest substances are, however, surprisingly stable at ambient temperatures and up to at least 95% humidity. Remarkably, the incorporation of even 10% (w/v) of extremely hygroscopic guest substances, such as the synthetic corticosteroid 6α,9α-difluoro-11β,21-dihydroxy-16α,17α-propyl methylene dioxy-4-pregnene-3,20-dione (XPDO), yields HDC glasses that are stable when exposed to relative humidities of up to 95% at room temperature for over a month, yet immediately release the guest substances within 5–10 mins when added to liquid water. An identical effect on HDC glass stability was found in TOAC glasses containing 10% (w/v) CSA incorporated as a guest.

We have also now found that adding other HDCs at these same levels also produced mixed HDC glasses that were equally resistant to devitrification at 95% relative humidity. Thus TOAC glasses containing 10% (w/v) of either GPAC or TOPR showed complete resistance to devitrification at 95% relative humidity. Interestingly, these composite HDC glasses behaved differently in liquid water; the GPAC/TOAC glass devitrified from the surface much faster than the TOPR/TOAC glass. See FIGS. 13, 14. This ability to tailor the dissolution rates of composite HDC glasses make them particularly useful as controlled release delivery vehicles.

The HDC glasses can be formed either from evaporation of the solvent or by quenching of the HDC melt. Because of the low softening points of certain HDC glasses, thermally labile guest substances such as drugs and biological molecules can be incorporated into the HDC melt during processing of the delivery system without decomposition. Surprisingly, these guest substances have demonstrated zero order release kinetics when the amorphous matrix forming compositions erode in aqueous solution. Release follows the process of surface devitrification. The HDC delivery systems can be easily modelled into any shape or form, such as those described herein. Such modelling can be by extrusion, molding etc. by any method known in the art. The HDC delivery vehicles are non-toxic and inert to any solutes which may be incorporated therein.

These HDC delivery systems, when formulated as matrices and/or coatings, undergo heterogeneous surface erosion when placed in an aqueous environment. While not being bound by any one theory, one possible mechanism for their degradation begins with an initial surface devitrification as supersaturation occurs at the interface, followed by subsequent erosion and/or dissolution of the surface layers at a slower rate. The matrices can be modified by careful selection of components to give the desired devitrification rates and hence the required release rates of the guest substance as the devitrified matrix provides no barrier to the release of the guest.

The HDC melts are excellent solvents for many organic molecules. This makes them particularly suitable for use in delivery of bioactive materials otherwise difficult to formulate. More than 20% weight percent of organic molecules can be incorporated into the HDC delivery systems. Notably, HDCs are inert and show no reactivity to their solutes or guest substances incorporated therein. As described in more detail below, the HDCs are suitable for forming a dispersion of a fine suspension of a SP delivery system to yield complex, composite delivery systems.

Component HDCs are synthesized to high purity using established chemical or enzymic synthetic principles. The HDCs and guest substances may be intimately mixed together in the appropriate molar ratios and melted until clear. Suitable melting conditions include, but are not limited to, melting in open glass flasks between 100 and 150° C. for 1–2 minutes. This results in a fluid melt which may be allowed to slightly cool before, dissolving the guest in the melt if required, quenching to glass for instance by pouring over a brass plate or into a metal mould for shaped delivery vehicles. Either way, melt temperature can be carefully controlled and guest substances can be incorporated into either the pre-melted HDC formulation, or stirred into the cooling HDC melt before quenching.

The HDC melts are thermally stable and allow the incorporation of organic molecules without denaturation or suspension of core particles without alteration of their physical nature. The glass melts can also be used to coat micron-sized particles, this is particularly important in the formulation of non-hygroscopic powders containing hygroscopic actives, for by-inhalation administration of therapeutic agents.

Alternatively, vitreous HDC delivery vehicles can be formed by evaporation of the HDC and guest to be incorporated in solution in a solvent or mixture of solvents. Component HDCs are readily dissolved in many organic solvents. Suitable solvents include, but are not limited to, dichloromethane, chloroform, dimethylsulfoxide (DMSO), dimethylformamide (DMF) and higher alcohols. The nature of the solvent is immaterial as it is completely removed on formation of the delivery system. Preferably both the component HDC and guest substance are soluble in the solvent. However, the solvent may dissolve the HDC and allow a suspension of the guest substance. On concentrating the solvent, crystallization does not occur with the more useful HDCs. Instead, an amorphous solid is produced, which has similar properties to the quenched glass. Again, guest substances can be easily incorporated either from solution or as a particle suspension.

HDC glass transition temperatures (Tg) are low, typically less than 70° C. and, surprisingly, are not predictable from the melt temperatures. In general, the tendency to crystallize, from a cooling melt or with reducing solvent, is low. Both devitrification and the fluidity of the melt at temperatures close to Tg, can be controlled by modifiers such as other derivative sugars and certain organic actives. The following two tables, generated as described in the Examples presented below, provide Tg and melting temperature data for a variety of HDCs suitable for use, either alone, or in a composite glass, herein.

TABLE 1

| Material/Glass | M.Pt./° C. | Tg/° C. | M.Wt |
|---|---|---|---|
| SHAC | 100–104 | −6 | 434.4 |
| α-GPAC | 109–111 | 14 | 390.3 |
| β-GPAC | 130–131 | 17 | 390.3 |
| OGTA | 50–52 | −10 | 460.5 |
| TOAC | 101–103 | 50 | 678.6 |
| TOPR | 47–48 | 3 | 790.6 |
| SOAC | 87–89 | 25 | 678.6 |
| COAC | 224–226 | 65 | 678.6 |
| RUDA | 87–88 | 55 | 966.9 |

TABLE 2

| Glass System | Mole ratios HDCs in glass | Tg/° C. |
|---|---|---|
| TOAC | 100 | 50 |
| RUDA | 100 | 55 |
| α-GPAC:TOAC | 10:90 | 47 |
| | 25:75 | 44 |
| | 50:50 | 32 |
| | 75:25 | 22 |
| SOAC:TOAC | 25:75 | 41 |
| COAC:TOAC | 25:75 | 55 |
| TOPR:TOAC | 22:78 | 37 |
| RUDA:TOAC | 10:90 | 52 |
| | 25:75 | 53 |
| | 50:50 | 52 |
| | 75:25 | 54 |

The invention further encompasses delivery vehicles comprising combinations of different HDCs which have now been found to provide novel delivery vehicles with highly controllable Tg and other physicochemical properties such as viscosity and resistance to aqueous degradation.

Combination Delivery Systems

The invention also encompasses solid dose delivery systems comprising HDCs and SPs and/or other glass forming substances in coformulations and other combinations. These are termed "combination delivery systems".

At least two combination delivery systems are produced by the coformulation of HDC and SP vehicles to produce the delivery systems. In one instance, microspheres of the SP delivery system are suspended within the HDC delivery system. In the second instance, microspheres of the HDC delivery system are suspended in the SP delivery system. These combination delivery systems allow release of at least two different guests, one hydrophobic and one hydrophilic, at least two different release rates.

Other combination delivery systems are formed by coating one delivery system with another. For instance, an SP delivery system in implantable form could be coated with a layer of HDC or HDC delivery system to provide delayed release of the guest substance in the SP delivery system or sequential release of different guest substances. A variety of such forms can be readily envisioned. The number of coatings is theoretically unlimited and is within the skill of one in the art to determine.

The combination delivery systems may also be formed by extruding a hollow cylindrical vehicle containing a lumen from a delivery vehicle or system (SP, HDC or combination) and filling the lumen with another delivery system. These compositions are particularly suited for formation of injectable or implantable devices.

Other Components in the Delivery Systems Other Glasses

As discussed below, the delivery systems may further contain at least one physiologically acceptable glass. Suitable glasses include, but are not limited to, carboxylate, phosphate, nitrate, sulfate, bisulfate, HDCs and combinations thereof. Carboxylates have previously been used where slowly water soluble glasses are required as many of these are only poorly soluble in water. Suitable such glasses include, but are not limited to, those described in PCT/GB 90/00497. However, the formation of these carboxylate glasses has previously only been done by quenching of the melt. The elevated temperature necessary to melt the carboxylates severely limits the carboxylates that can be used to form vitreous delivery vehicles, particularly in the case of bioactive materials which tend to be heat labile. We have now found, surprisingly, that carboxylate glasses can be easily formed by evaporation of a solvent containing the glass-forming metal carboxylate and guest substance to be incorporated. The invention thus encompasses methods of making solid dose vehicles and systems comprising dissolving a carboxylate component in a suitable solvent therefor and evaporating the solvent to yield a vitreous glass. Mixtures of carboxylates can be used as can mixtures of other glass-forming components to produce novel delivery systems which are encompassed by the present invention.

The delivery systems may also be coated with one or more layers of a physiologically acceptable glass having a predetermined solution rate. This is especially effective for pulsatile release of guest substances. The composition may further contain other water soluble and biodegradable glass formers. Suitable glass formers include, but are not limited to, lactide and lactide/glycolide copolymers, glucuronide polymers and other polyesters, polyorthoesters, and polyanhydrides.

Guest Substances Examples of types of guest substances that may be used in the vehicle and methods of the invention include industrial chemicals such as dyes and perfumes and medicinal or agricultural bioactive materials suitable for use in vivo and in vitro. Suitable bioactive materials include, but are not limited to, pharmaceutical agents, therapeutic and prophylactic agents and agrochemicals such as pesticides and pheromones.

Suitable pharmaceutical agents, include, but are not limited to, antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs, opioids, and the like.

Suitable therapeutic and prophylactic agents include, but are not limited to, any therapeutically effective biological modifier. Such modifiers include, but are not limited to, subcellular compositions, cells, bacteria, viruses and molecules including, but not limited to, lipids, organics, proteins and peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein-nucleic acid hybrids, small molecules and physiologically active analogs thereof. Further, the modifiers may be derived from natural sources or made by recombinant or synthetic means and include analogs, agonists and homologs.

As used herein "protein" refers also to peptides and polypeptides. Such proteins include, but are not limited to, enzymes, biopharmaceuticals, growth hormones, growth factors, insulin, monoclonal antibodies, interferons, interleukins and cytokines.

Organics include, but are not limited to, pharmaceutically active chemicals. For instance, representative organics include, but are not limited to, vitamins, neurotransmitters, antimicrobials, antihistamines, analgesics and immunosuppressants.

Suitable steroid hormones include, but are not limited to, corticosteroids, estrogen, progesterone, testosterone and physiologically active analogs thereof. Numerous steroid hormone analogs are known in the art and include, but are not limited to, estradiol, SH-135 and tamoxifen. Many steroid hormones such as progesterone, testosterone and analogs thereof are particularly suitable for use in the present invention as they are not absorbed transdermally and, with the exception of a few analogs, are destroyed upon oral administration by the so-called hepatic first pass mechanism.

As used herein, "nucleic acids" includes any therapeutically effective nucleic acids known in the art including, but not limited to, DNA, RNA and physiologically active analogs thereof. The nucleotides may encode single genes or may be any vector known in the art of recombinant DNA including, but not limited to, plasmids, retroviruses and adeno-associated viruses. Preferably, the nucleotides are administered in the powder form of the solid dose system.

Compositions comprising solid dose delivery systems containing prophylactic bioactive materials and carriers therefore are further encompassed by the invention. Preferable compositions include immunogens such as for use in vaccines. Preferably, the compositions contain an immunogenic amount of the immunogen effective for either immunization or booster inoculation.

Suitable immunogens include, but are not limited to, live and attenuated viruses, nucleotide vectors encoding antigens, bacteria, antigens, antigens plus adjuvants, and haptens coupled to carriers. Particularly preferred are immunogens effective in causing an immune response against diphtheria, tetanus, pertussis, botulinum, cholera, Dengue, Hepatitis A, C and E, hemophilus influenza b, herpes virus, *Helicobacterium pylori,* influenza, Japanese encephalitis, meningococci A, B and C, measles, mumps, papilloma virus, pneumococci, polio, rubella, rotavirus, respiratory syncytial virus, Shigella, tuberculosis, yellow fever and combinations thereof.

Immunogens may also be produced by molecular biology techniques to produce recombinant peptides or fusion proteins containing one or more portions of a protein derived from a pathogen. For instance, fusion proteins containing the antigen of interest and the B subunit of cholera toxin have been shown to induce an immune response to the antigen of interest. Sanchez et al. (1989) *Proc. Natl. Acad. Sci. USA* 86:481–485.

Preferably, the immunogenic composition contains an amount of an adjuvant sufficient to enhance the immune response to the immunogen. Suitable adjuvants include, but are not limited to, aluminum salts, squalene mixtures (SAF-1), muramyl peptide, saponin derivatives, mycobacterium cell wall preparations, monophosphoryl lipid A, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) *Nature* 344:873–875. For veterinary use and for production of antibodies in animals, mitogenic components of Freund's adjuvant can be used.

As with all immunogenic compositions, the immunologically effective amounts of the immunogens must be determined empirically. Factors to be considered include the immunogenicity, whether or not the immunogen will be complexed with or covalently attached to an adjuvant or carrier protein or other carrier, route of administration and the number of immunizing doses to be administered. Such factors are known in the vaccine art and it is well within the skill of immunologists to make such determinations without undue experimentation.

Preferably, if the guest substance and/or vehicle contain carboxyl and amino, imino or guanidino groups, the delivery systems further comprise at least one physiologically acceptable inhibitor of the Maillard reaction in an amount effective to substantially prevent condensation of amino groups and reactive carbonyl groups in the composition.

The inhibitor of the Maillard reaction can be any known in the art. The inhibitor is present in an amount sufficient to prevent, or substantially prevent, condensation of amino groups and reactive carbonyl groups. Typically, the amino groups are present on the bioactive material and the carbonyl groups are present on the carbohydrate, or the converse. However, the amino and carbonyl groups may be intramolecular, within either the biological substance or the carbohydrate. Various classes of compounds are known to exhibit an inhibiting effect on the Maillard reaction and hence to be of use in the compositions described herein. These compounds are generally either competitive or noncompetitive inhibitors. Competitive inhibitors include, but are not limited to, amino acid residues (both D and L), combinations of amino acid residues and peptides. Particularly preferred are lysine, arginine, histidine and tryptophan. Lysine and arginine are the most effective. There are many known noncompetitive inhibitors. These include, but are not limited to, aminoguanidine and derivatives, are 4-hydroxy-5,8-dioxoquinoline derivatives and suitable Maillard inhibitors such as those in EP-A-O 433 679.

Dosage Forms

In addition to the dosage forms described above, a variety of other dosage forms suitable for different uses are provided herein.

The invention encompasses delivery systems that are sized and shaped for penetration of the epidermis and are suitable for ballistic delivery. Suitable vehicle size is thus on the order of microns, preferably in the range of 1–5 microns in diameter and 5–150 microns in length, which allows penetration and delivery through the epidermis to subcutaneous and intradermal, intramuscular, intravenous tissues. It will be appreciated that, at this size, the delivery system may macroscopically appear to be in powder form, regardless of its configuration at the microscopic level.

Preferred configurations of the ballistic delivery systems are microneedles and microfibers. The manufacture of microfibers is relatively simple and economical and results in stable delivery systems comprised of the vehicle in glassy form and the guest substance. Additional stabilizers, buffers, glasses and polymers may also be added during processing as described herein. Many of the most labile biomolecules can withstand high temperatures (e.g., 60–100° C.) when stabilized by drying in trehalose, provided that the majority of their surface is in contact with the vehicle. Temperatures of 70° C. can be tolerated for over a month (Colaco et al. (1992) *Bio/Technology* 10:1007–1011) and higher temperatures for shorter periods. The results presented herein show that the fluorescent protein phycoerythrin dried in trehalose can be stored at 100° C. for at least one month with no detectable loss of functional activity. Other vehicles give protection at lower temperatures than trehalose. The maximum temperature of protection must be determined empirically and is within the skill of one in the art without undue experimentation.

The microfibers prepared in accord with the principles of the present invention have a relatively high aspect ratio, i.e., length compared to diameter, preferably in the range of 1–5 microns in diameter and 5–150 microns in length. This high aspect ratio provides for enhanced "end on" penetration upon ballistic delivery, by the tendency of the microfibers to line up parallel to the barrel of the ballistic microinjector, as described in more detail below. Longer macrofibers may be injected using conventional impact ballistic devices or by trocar. Alternatively, macroscopic glass needles of sufficient intrinsic strength may be directly driven in through the skin for subcutaneous, intradermal or intramuscular administration of the guest substance.

Alternative preferred embodiments of the delivery systems include uniform microspheres, preferably with a narrow size distribution. This configuration is particularly useful when increased control of the depth of penetration of the delivery system is desirable. Such control would be useful, for example, for intradermal, intramuscular, intravenous delivery of vaccines to the basal layer of the epidermis, to bring antigen into proximity to the Langerhans cells of the skin to induce optimal immune responses.

The invention also encompasses hollow fibers for delivery of guest substances. By drawing down a hollow billet through a zone furnace which produces local softening of the vitreous vehicle, fine hollow needles can be formed. These needles can be filled with a finely powdered stabilized compound by introduction of the fine powder during the melting and drawing down process. The hollow fiber can also be made of thermoplastic, organic polymer and/or carbohydrate and/or HDC which may itself be slowly or rapidly water soluble and/or biodegradable.

An alternative embodiment of the delivery vehicle in the invention comprises a hollow vehicle comprised of poorly water soluble glass or plastic which is filled and optionally coated the delivery systems described herein.

In another embodiment of the invention, coformulations of vehicles and other poorly water soluble materials are included. For example, coformulations of vehicles with water-soluble glasses such as phosphate, nitrate or carboxylate glasses or biodegradable plastics such as lactide or lactide/glycolide copolymers will yield a more slowly eroding vehicle for delayed release of the bioactive material.

Methods of Making the Delivery Systems

The invention further encompasses methods of making the solid dose systems. Providing the exposure time is limited, guest substances admixed in dry vehicles can be heated to fluidize the glass which can then be drawn or spun as a fiber without damage to the product. Fibers can either be drawn from a billet, cooled to solidify them and then wound onto a drum or they can be spun through fine holes in a rapidly rotating cylinder that is heated above the melting point of the vehicle. Being inherently brittle, these fibers can be readily cut, broken, crushed or chopped into short lengths to form long cylindrical rods or needles. By varying the diameter of the fibers produced, needles can be formed which vary from micro to macro needles, i.e., from thicknesses of a few microns to fractions of a millimeter. It has been found that cotton candy machines are suitable for use in preparing the finer diameter microfibers. Although the optimal conditions must be determined empirically for each vehicle, such determinations are well within the skill of one in the art.

To prepare microspheres of the present invention, several methods can be employed depending upon the desired application of the delivery vehicles. Suitable methods include, but are not limited to, spray drying, freeze drying, air drying, vacuum drying, fluidized-bed drying, milling, co-precipitation and super-critical fluid evaporation. In the case of spray drying, freeze drying, air drying, vacuum drying, fluidized-bed drying and super-critical fluid evaporation, the components (SP and/or HDC, and/or other glass former, guest substances, buffers etc.) are first dissolved or suspended in suitable solvents. In the case of milling, glasses formed from the components, either by solvent evaporation or quenching of the melt, are milled in the dried form and processed by any method known in the art. In the case of co-precipitation, the components are mixed in organic conditions and processed as described below.

Spray drying can be used to load the vehicle with the guest substance. The components are mixed under suitable solvent conditions and dried using precision nozzles to produce extremely uniform droplets in a drying chamber. Suitable spray drying machines include, but are not limited to, Buchi, NIRO, APV and Lab-plant spray driers used according to the manufacturer's instructions. A number of carbohydrates are unsuitable for use in spray drying as the melting points of the carbohydrates are too low, causing the dried amorphous materials to adhere to the sides of the drying chamber. Generally, carbohydrates with a melting point of less than the operating temperature of the spray drying chamber are unsuitable for use in spray drying. For example, palatinit and lactitol are not suitable for use in spray drying under conventional conditions. A determination of suitable carbohydrates can thus be made on known melting points or determined empirically. Such determinations are within the skill of one in the art.

An alternative method for manufacturing microspheres as delivery vehicles in accord with the present invention is to prepare a uniform aqueous/organic phase emulsion of the guest substance in a solution of the vehicle as the aqueous phase and a glass former in the organic phase or the converse. This is followed by drying of the emulsion droplets to form a solid solution of the guest substance and vehicle in an amorphous matrix of the glass former. In a modification of this method, the emulsion may be formed from the guest substance in solid solution in the vehicle and two different glass formers and/or polymers dissolved together in one solvent, or dissolved into two separate solvents. The solvent(s) are then removed by evaporation to yield double or multi-walled microspheres. Suitable methods for making multi-walled microspheres are described, for instance, in Pekarek et al. (1994) *Nature* 367:258–260; and U.S. Pat. No. 4,861,627.

The delivery system can also be dried from an organic solution of an SP and a hydrophobic guest substance to form a glass containing homogeneously distributed guest substance in solid solution or fine suspension in the polyol glass. These glasses can then be milled and/or micronized to give microparticles of homogeneous defined sized.

The guest substance and vehicle can also be co-precipitated to give high quality powders. Co-precipitation is performed by spraying, for instance with an air brush, the various components and/or polymeric glass former into a liquid in which neither dissolves, such as ice-cold acetone.

The invention also encompasses hollow fibers for delivery of guest substances. By drawing down a heated hollow billet, fine hollow needles can be formed. These can be made to contain a finely powdered stabilized compound by introduction of the fine powder during the melting and drawing down process. The hollow fiber can also be made of thermoplastic, organic polymer and/or carbohydrate and/or HDC glass which may itself be slowly or rapidly water soluble and/or biodegradable.

An alternative embodiment of the delivery vehicle in the invention comprises a hollow vehicle comprised of poorly water soluble glass or plastic which is filled and optionally coated with SP and/or HDC glass and the guest substance. Fine hollow fibers of slowly water-soluble inorganic or organic glasses can be drawn from a hollow billet and a finely powdered SP delivery system can be incorporated into the lumen of the billet, and therefore of the fiber, during the process.

In another embodiment of the invention, coformulations of vehicles and other water soluble materials are included. For example, coformulations of vehicles with water-soluble glasses such as phosphate glasses (Pilkington Glass Company) or biodegradable plastics such as lactide or lactide/glycolide copolymers will yield a more slowly eroding vehicle for delayed release of the guest substance. To produce the coformulations, a finely powdered glass containing the guest substance can be intimately mixed with a finely powdered carboxylate glass and co-sintered. Alternatively, if a metal carboxylate glass has a lower melting point than the delivery system, the latter can be homogeneously embedded as an encapsulate in a carboxylate glass on quenching of the melt obtained. This can be milled to give a fine powder with solubilities intermediate between the relatively rapid solubility of the vehicle and the slow solubility of the carboxylate glass.

Alternate coformulations include the use of a homogeneous suspension of the finely powdered vitreous delivery system encapsulated in a carboxylate glass by drying from an organic solvent in which the carboxylate is soluble, but the amorphous powder is not, to form the carboxylate glass. This can be ground to give a fine powder which would have the relatively rapidly dissolving delivery system entrapped within a slow dissolving carboxylate glass (i.e., comparable to a conventional slow-release system). Pulsatile release formats can be achieved either by repeated encapsulation cycles using glasses of different dissolution rates, or by mixing powders of a number of coformulations with the desired range of release characteristics. Note that this glass could also be drawn or spun to give microfibers or microneedles which would be slow-release implants. It will be appreciated that any delivery system formulation should be such that it is capable of releasing the guest substance upon administration, and should not unduly effect the stability of the material being administered.

As discussed above, glasses of derivatized carbohydrates are also suitable for use herein. Suitable derivatized carbohydrates include, but are not limited to, carbohydrate esters, ethers, imides and other poorly water-soluble derivatives and polymers.

The delivery vehicle can be loaded with the guest substance by drying a solution of the guest substance containing a sufficient quantity of vehicle to form a glass on drying. This drying can be accomplished by any method known in the art, including, but not limited to, freeze drying, vacuum, spray, belt, air or fluidized-bed drying. The dried material can be milled to a fine powder before further processing the material with the polyol glass or coformulation.

Different dosing schemes can also be achieved depending on the delivery vehicle employed. A delivery vehicle of the invention can provide for a quick release or flooding dose of the guest substance after administration, where the delivery system is readily soluble. Coformulations of vehicles with slowly water soluble glasses and plastics such as phosphate, nitrate or carboxylate glasses and lactide/glycolide, glucuronide or polyhydroxybutyrate plastics and polyesters, can provide more slowly dissolving vehicles for a slower release and prolonged dosing effect. A priming and booster effect can also be realized by utilizing a hollow, slowly water soluble vehicle filled and coated with a rapidly dissolving SP and/or HDC glass loaded with the guest substance. The glass coating loaded with the guest substance will dissolve rapidly to give an initial dosing effect. There will be no dosing action while the hollow outer wall portion of the vehicle dissolves, but the initial priming dose will be followed by a booster dose of the inner filling when the hollow outer wall is breached by dissolution. Such pulsatile release format is particularly useful for delivery of immunogenic compositions. Should multiple effect pulsatile delivery be desirable, delivery vehicles with any combination of layers of "non-loaded" vehicles and vehicles loaded with the guest substances can be constructed.

The delivery of more than one guest substance can also be achieved using a delivery system comprised of multiple coatings or layers of the vehicle loaded with different materials or mixtures thereof. Administration of the solid dose delivery systems of the present invention can be used in conjunction with other conventional therapies and coadministered with other therapeutic, prophylactic or diagnostic substances.

Methods of Delivery

The invention further encompasses methods of delivery of the solid dose systems.

Suitable delivery methods of guest substances include, but are not limited to, topical, transdermal, transmucosal, oral, gastrointestinal, subcutaneous, ocular, intramuscular, intravenous and by-inhalation (naso-pharyngeal and pulmonary, including transbronchial and transalveolar). Topical administration is, for instance, by a dressing or bandage having dispersed therein a delivery system, or by direct administration of a delivery system into incisions or open wounds. Creams or ointments having dispersed therein slow release bead or microspheres of a delivery system are suitable for use for instance as topical ointments or wound filling agents.

Compositions for transdermal administration are preferably powders of delivery systems in the form of homogeneously sized microneedles or microbeads. Larger, macroscopic needle and bead forms of the delivery systems are also provided for subdermal implantation and extended drug delivery. The particle sizes should be small enough so that they cause only minimal skin damage upon administration. The powder forms of the delivery systems can be microneedles of approximately 10–1,000 microns in length and 1–150 microns in diameter. The powders may be prepackaged in single-dose, sealed, sterile formats.

Suitable methods of transdermal administration include, but are not limited to, direct impact, ballistic, trocar and liquid jet delivery. For direct impact delivery, macroneedles can be precision-formed by methods well known in the inorganic glass forming art, such as those used for optical fibre production. These needles could be housed in a precision formed closed fitting plastic barrel and driven directly through the skin by a plunger. Ballistic administration is preferred as it is relatively painless. Generally the delivery system is accelerated in a shock wave of helium or another gas and fired into the epidermis. A suitable device for ballistic delivery is described in PCT/GB 94/00753. A suitable device for liquid-jet delivery is a Mediject device (*Diabetes Care* (1993) 1b, 1479–1484). Such liquid-jet devices are particularly useful with the larger macroneedle delivery systems which may also be delivered by the use of conventional impact ballistic devices or by trocar.

Upon transdermal administration, the degree of penetration of the delivery system can be controlled to a certain degree, not only by the ballistic microinjector, described below, but also by the shape and size of the powder particles. For example, when a relatively uniform and lesser degree of penetration is desirable, microspheres may be more suitable for the practice of the present invention. When a greater degree of penetration is desirable, a microneedle configuration may be preferred.

Because the aspect ratio (i.e., length to diameter) of the microneedles is high, they have higher masses than spherical particles with a similar diameter. If they can be induced to impact with the skin "end-on," their higher mass will give them a higher momentum for the same velocity and they will thus penetrate deeper into the tissues. When randomly oriented microneedles are put into a laminar flow of gas, they will align themselves in the direction of the air flow and in the gas-propelled ballistic injector this will ensure that they impact the skin at right angles to ensure penetration.

The delivery systems suitable for transmucosal delivery include, but are not limited to, mucoadhesive wafers, films or powders, lozenges for oral delivery, pessaries, and rings and other devices for vaginal or cervical delivery.

Compositions suitable for gastrointestinal administration include, but are not limited to, pharmaceutically acceptable powders, tablets, capsules and pills for ingestion and suppositories for rectal administration.

Compositions suitable for subcutaneous administration include, but are not limited to, various implants. Preferably the implants are macroscopic discoid, spherical or cylindrical shapes for ease of insertion and may be either fast or slow release. Since the entire implant is dissolved in the body fluids, removal of the implant is not necessary. Furthermore, the implants do not contain synthetic polymers and are biodegradable.

Compositions suitable for ocular administration include, but are not limited to microsphere and macrosphere formulations and saline drops, creams and ointments containing these and round-ended shaped rods which fit comfortably in the lower conjunctival fornix beneath the lower eyelid.

Compositions suitable for by-inhalation administration include, but are not limited to, powder forms of the delivery systems. Preferably the powders are of a particle size 0.1 to 10 microns. More preferably, the particle size is 0.5 to 5 microns. Most preferably, particle size is 1 to 4 microns. In particular for pulmonary administration, the preferred particle size is 2.5–3 microns.

Preferably SP delivery vehicle powders also contain an effective amount of a physiologically acceptable molecular water pump buffer (MWPB). A MWPB is a physiologically acceptable salt that effects a loss of water from the composition so that at ambient humidity the vapor pressure of water of crystallization is at least 14 mm Hg (2000 Pa) at 20° C. and does not interfere with glass formation of the vehicle. An effective amount of an MWPB is one which sufficiently reduces hygroscopicity to prevent substantial clumping, for instance, a 50% molar ratio of potassium sulfate. Sodium sulfate and calcium lactate are the preferred salts with potassium sulfate being the most preferred.

The composite HPC delivery systems are particularly useful for by-inhalation dosage forms. For instance, 10% (w/v) αGPAC/TOAC mixed delivery systems are resistant to 95% relative humidity (RH) but recrystallize on contact with liquid water and thus release any guest substances incorporated therein. This is especially important for inhalable powders as these powders would preferably devitrify and release guest substances upon hitting liquid in the alveoli and not in the humid tracheal airways.

Atomizers and vaporizers filled with the powders are also encompassed by the invention. There are a variety of devices suitable for use in by-inhalation delivery of powders. See, e.g., Lindberg (1993) *Summary of Lecture at Management Forum* 6–7 December 1993 "Creating the Future for Portable Inhalers." Additional devices suitable for use herein include, but are not limited to, those described in WO9413271, WO9408552, WO9309832 and U.S. Pat. No. 5,239,993.

Various other solid dose delivery systems are encompassed by the invention. These are suitable for delivery of a wide variety of non-medical guest substances. For instance, an HDC glass, incorporating an agricultural guest substance is dry on the shelf, even in the tropics, but releases pesticide or biological control agents on contact with liquid water on plant surfaces or in the soil. An HDC glass incorporating an enzyme is useful in adding to laundry detergents as it stabilizes the enzyme even in high humidity yet releases the enzyme immediately on contact with water. Numerous other embodiments are encompassed by the claimed invention and are within the skill of one in the art to devise.

The following examples are provided to illustrate but not limit the present invention.

EXAMPLE 1

Methods of Making Microfiber SP Vitreous Solid Dose Delivery Systems a) SP Microfiber Formation Glasses were formed by drying 20% solutions of either trehalose, lactitol, palatinit or GPS, containing MWPB and 1 mg/ml of the fluorescent algal protein phycoerythrin under vacuum (80 mTorr) for 16 hrs. The glasses were ground in a domestic coffee mill to yield a coarse powder which was used to fill the spinning head of a Kando K1 Kandy Floss cotton candy machine (GB Patent No. 1533012). The motor was then switched on and the powdered sugar glass heated at element settings between 5 and 9. Residence time in the spinning head was 2–10 min and a continuous process was maintained by constantly topping up the head.

The fibers produced were ground in a domestic coffee grinder and the results obtained are presented in Table 3, which shows an average of the needles produced. These data indicate that, with all three sugar glasses, reduced element settings result in the production of finer diameter microneedles. With trehalose, setting 6 gave microneedles with a mean diameter of 15 microns, and setting 9, microneedles with a mean diameter of 40 microns. With GPS, setting 9 gave microneedles with a mean diameter of 15 microns. Microneedles formed from glasses containing buffer salts remained dry at ambient temperatures and humidities. Microneedles containing phycoerythrin showed retention of biological activity as assessed by fluorescence.

TABLE 3

|  | Microneedle size analysis | |
| --- | --- | --- |
|  | Length ($\mu$m) | Width ($\mu$m) |
| Mean | 192.60 | 43.35 |
| Standard Error | 12.53 | 2.33 |
| Median | 167.5 | 37.5 |
| Mode | 137.5 | 47.5 |
| Standard Deviation | 123.44 | 22.91 |
| Sample Variance | 15237.75 | 524.72 |
| Kurtosis | 16.17 | 2.55 |
| Skewness | 3.35 | 1.45 |
| Range | 862.5 | 115 |
| Minimum | 67.5 | 10 |
| Maximum | 930 | 125 |
| Sum | 18682.5 | 4205 |
| Count | 97 | 97 |
| Confidence Level (95.000%) | 24.57 | 4.56 | b) Binary SP/Organic Composite Glass Microfiber Formation

Glasses were formed by drying a 5:1:1 mixture of trehalose, sodium octanoate and water under vacuum (80 mTorr) for 16 hrs. The glasses were ground in a domestic coffee mill to yield a coarse powder which was used to fill the spinning head of a Kando K1 Kandy Floss machine. The motor was then switched on and the powdered binary carbohydrate/organic glass heated at element settings between 5 and 9. As with pure trehalose glasses, reduced element settings resulted in the production of finer diameter microneedles. The binary mixture glasses can be tailored to yield glasses with significantly different tensile properties compared to the corresponding pure trehalose glasses. Residence time in the spinning head was again 2–10 min and a continuous process was maintained by constantly topping up the head. The results obtained indicate that variations of the melting points and dissolution times of the glasses and the resulting physical properties of the microfibers can be achieved by varying both the carbohydrate/organic molecules and ratios used.

EXAMPLE 2

Figure 2A:
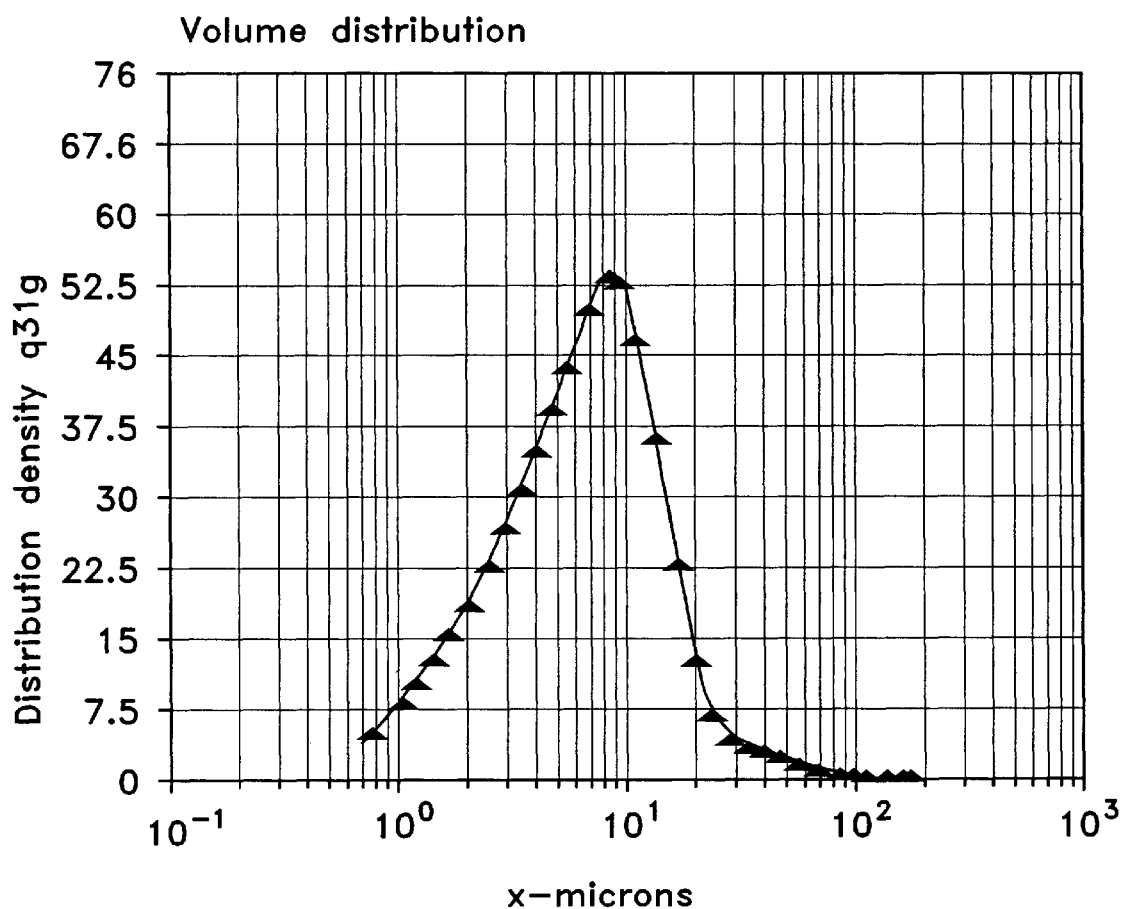
FIG. 2A is a graph depicting the narrow particle size distribution for trehalose/molecular water pump buffer salt (MWPB) glass powder.
Figure 2B:
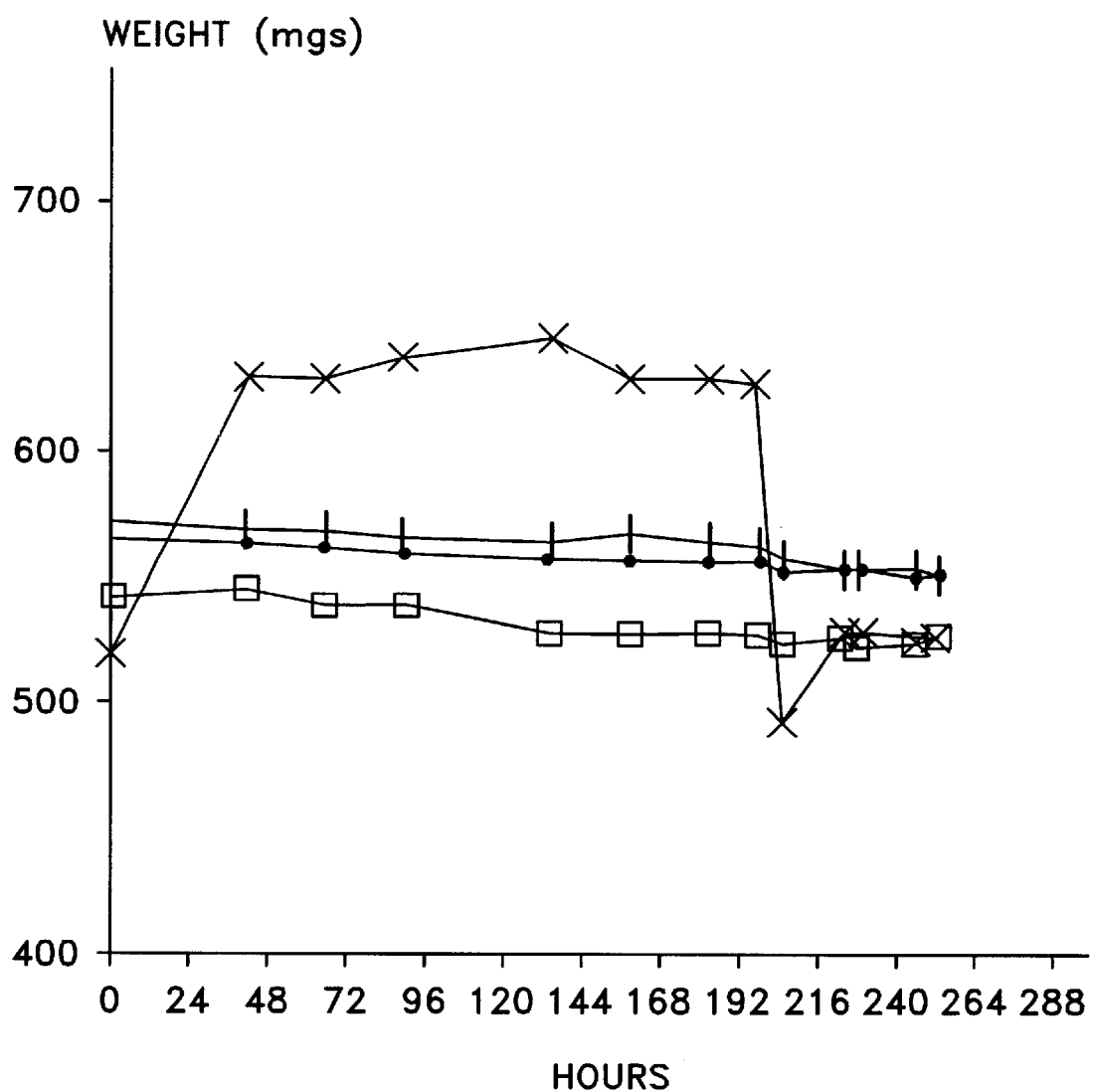
FIG. 2B is a graph depicting the water absorption of various
Figure 3:
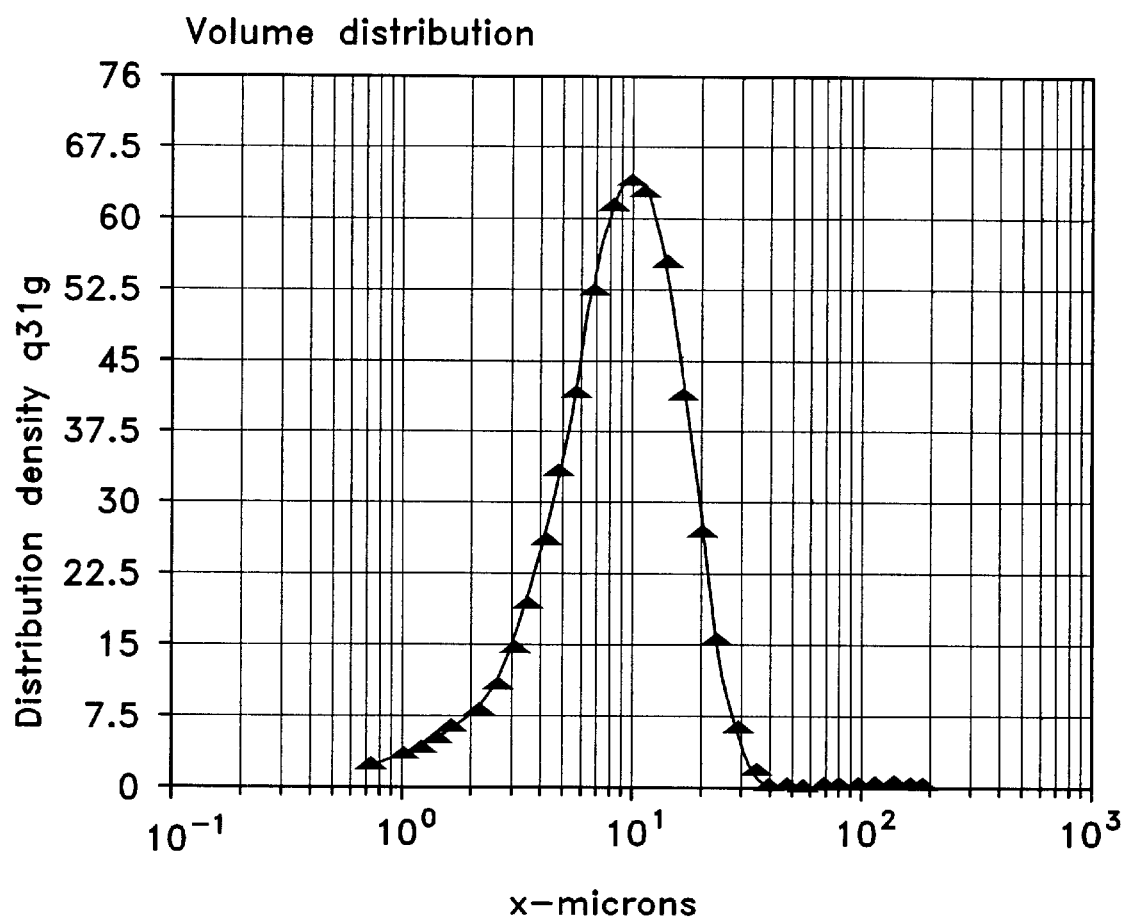
Figure 4:
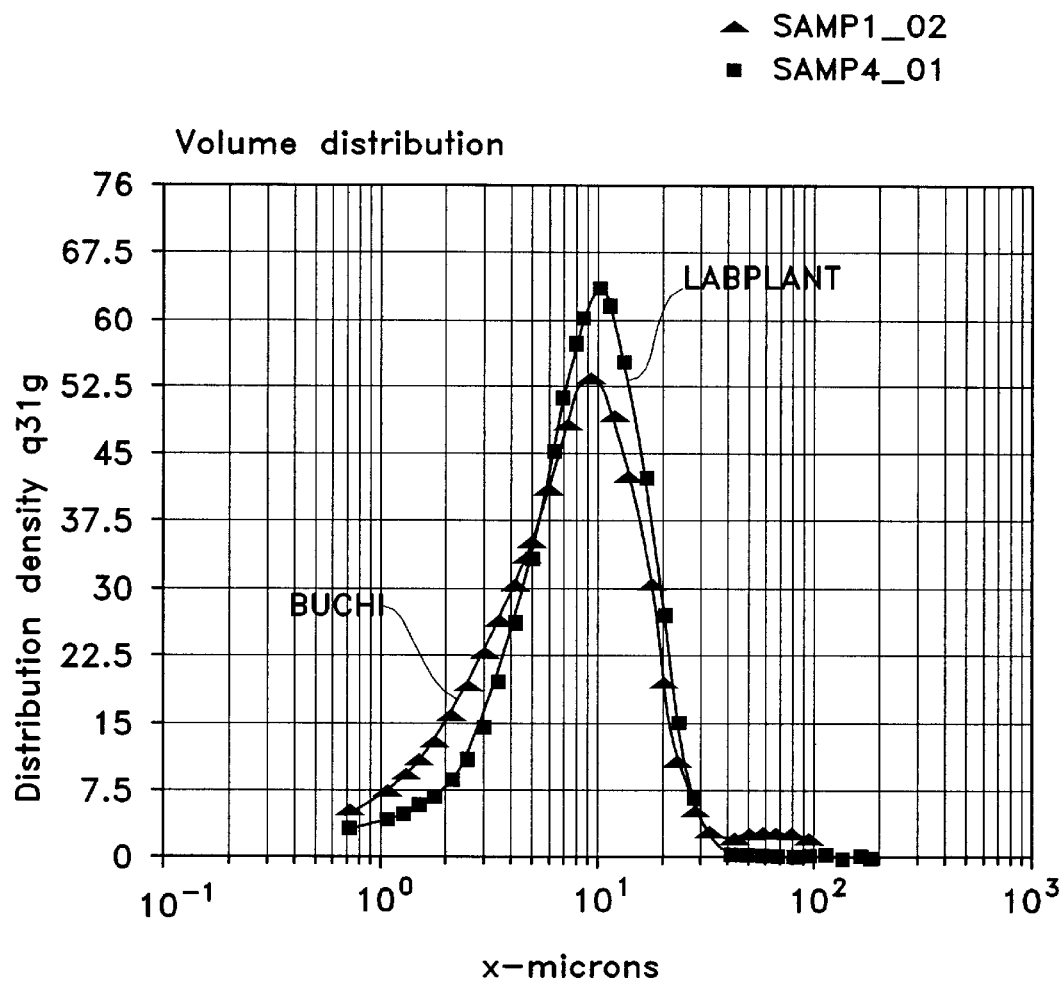
Figure 5A:
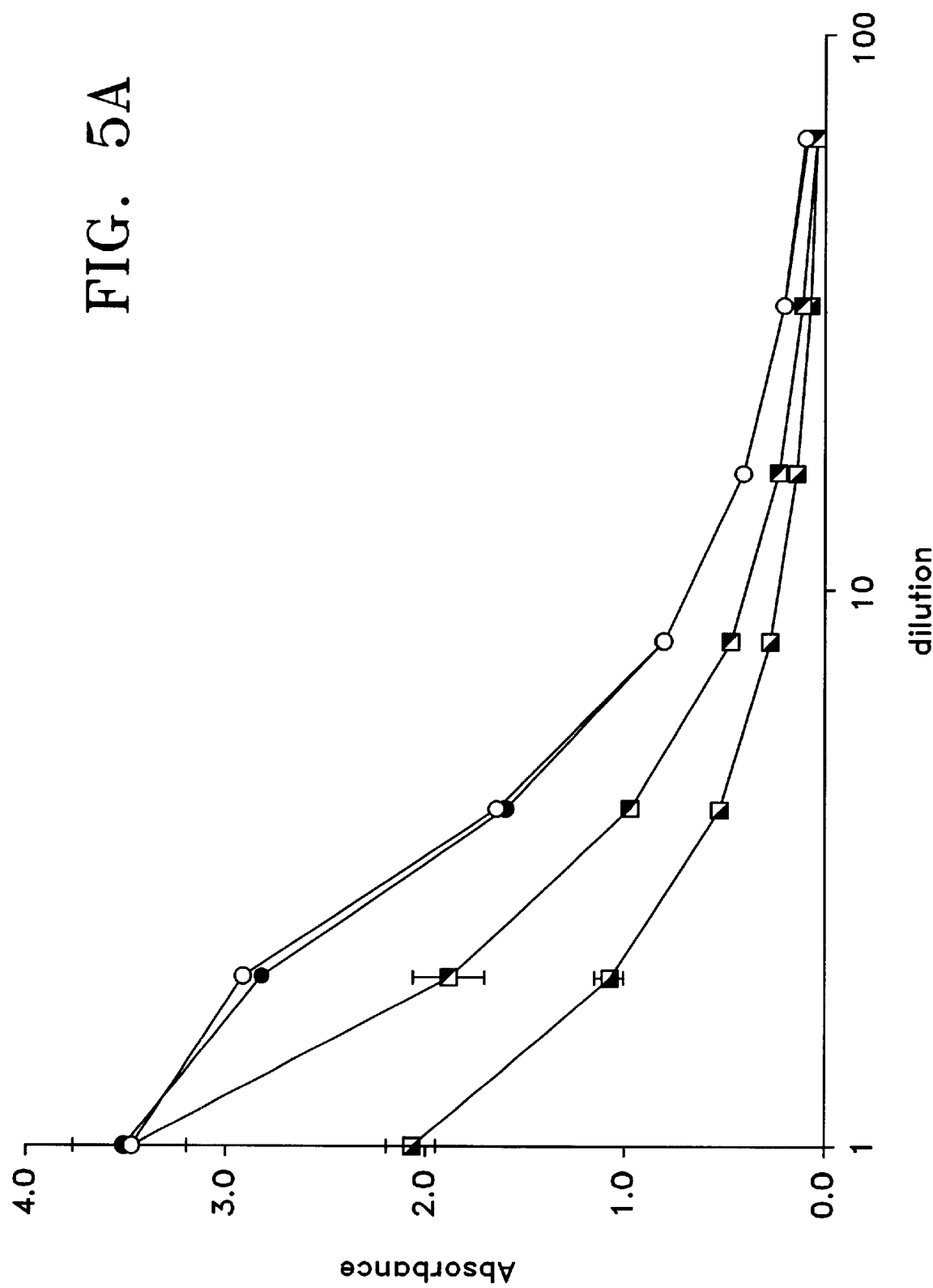
Figure 5B:
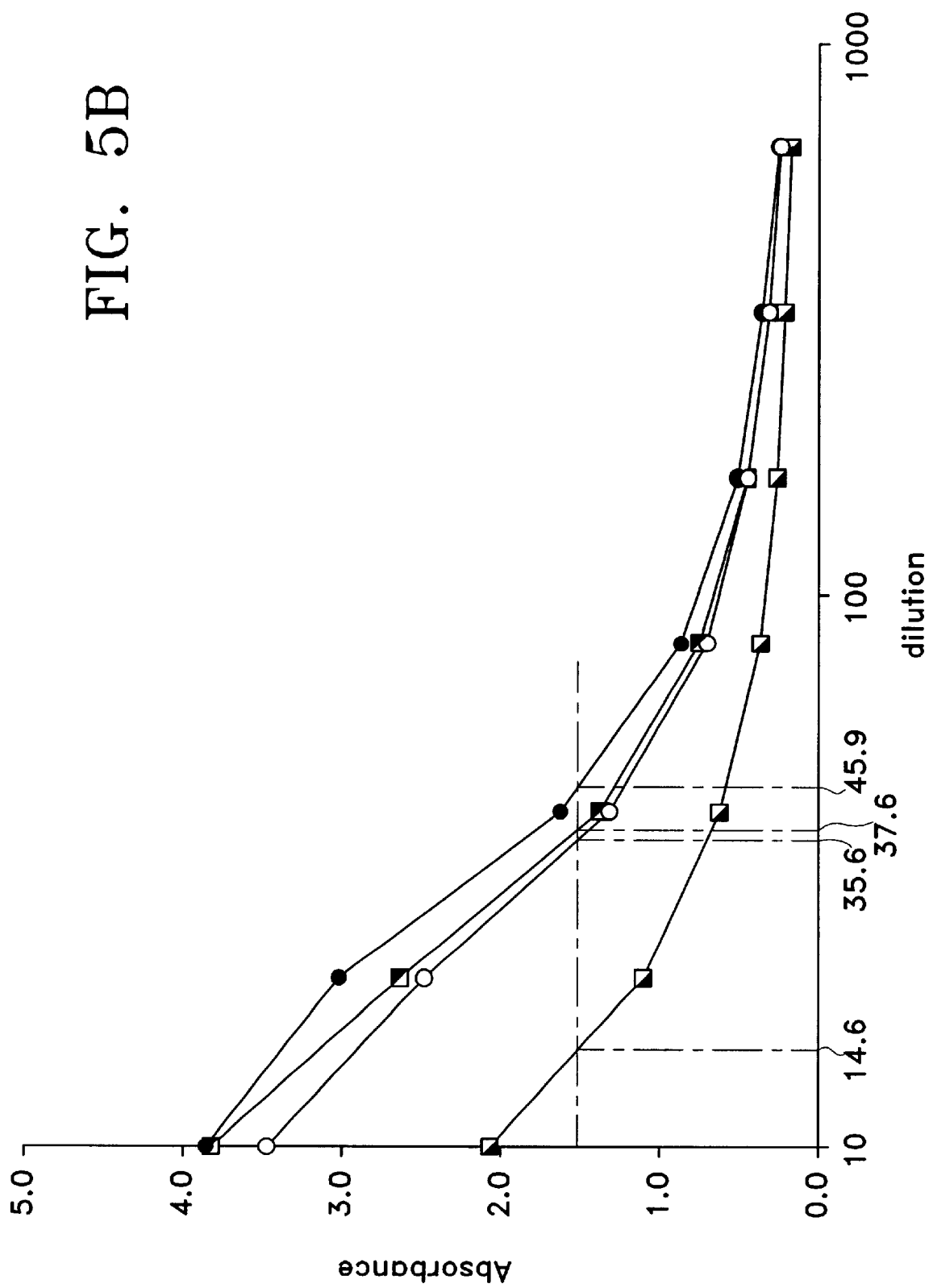
Figure 6:
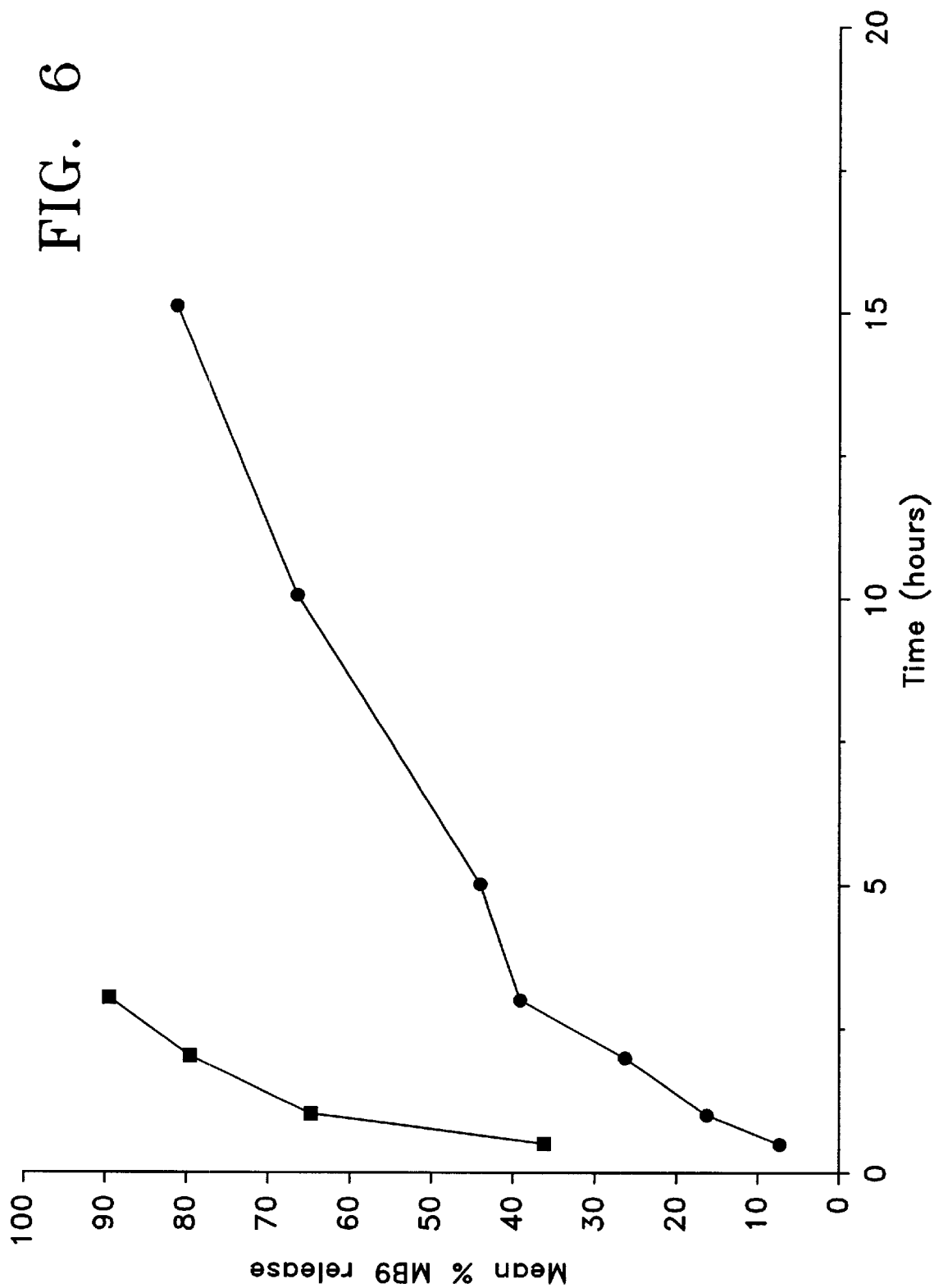

Methods of Making Powder SP Vitreous Solid Dose Delivery Systems a) Incorporation of Active in SP Vitreous Delivery Vehicle to Yield Micronized Powders Glasses were formed by drying 20% solutions of either trehalose, lactitol, palatinit, GPM or GPS, containing an equimolar ratio of MWPB and protein, by freeze-drying under vacuum (80 mTorr) for 16 hrs. The glasses were powdered using a Trost air-jet mill. Particle size in the micronized powders were measured using a Malvern Mastersizer laser particle sizer. The results obtained with micronized powders obtained from an original solution of 0.5 M trehalose and 0.5 M calcium lactate showed a monodisperse particle distribution with mean particle diameters of 1.1 microns (FIG. 1). The powders containing MWPB remained a free-flowing powder and showed no change in particle size or clumping and uptake of water on extended exposure to ambient temperatures and humidities (FIGS. 2A and 2B).

b) Incorporation of Active in SP Vitreous Delivery Vehicle to Yield Spray-dried Powders 20% solutions of trehalose containing MWPB salts and protein (phycoerythrin) were dried in a Buchi or Lab-Plant spray drier at a pump speed of 500–550 ml/hr and an inlet temperature of 180° C. Particle size was measured using a SympaTec laser particle sizer. The spray-dried powders showed a monodisperse particle distribution with a sufficiently narrow peak size distribution for effective use as particles in a powder ballistic device. In the results shown in FIG. 3, particle size analysis of a spray-dried powder produced by spray drying a mixture of 0.5 M trehalose and 0.5 M calcium lactate on a Lab-Plant spray drier showed a mean particle diameter of 8.55 microns and illustrates the tight peak distribution obtained. Variation of the mean particle size can be achieved by varying either the composition of the mixture to be spray dried or the characteristics of the spray drier nozzle assembly used. The results shown in FIG. 4 provide a comparison of the particle size analysis of the spray-dried powder as in FIG. 3 with a spray-dried powder produced by drying the same mixture on the Buchi spray drier which uses a different nozzle assembly. The peak distribution shown in FIG. 4 shows an equally narrow range but the mean particle size is now 7.55 microns.

These data show that the particles obtained by different spray-drying processes are equally suitable to provide compositions for ballistic delivery. Note that the ability to vary particle size results in compositions with different penetrative characteristics. This is particularly important for determining intradermal, intramuscular, intravenous or intramuscular delivery as the penetration is a function of particle momentum and the distribution is a function of the scatter of particle size.

c) Incorporation of Active in SP Vitreous Delivery Vehicle by Drying from Organic Solvents A 50 mg/ml solution of CSA in a 1.1 mixture of ethanol:water, containing 20% trehalose, was air-dried at ambient temperature to form a clear trehalose glass containing CSA in solid suspension or solution. The glass was ground to give a powder, according to the method described in Example 1, and remained a free-flowing powder at ambient temperature and humidities. Addition of the powder to water resulted in the dissolution of the trehalose and the formation of a uniform aqueous suspension of CSA.

d) Incorporation of Active in SP Vitreous Delivery Vehicle by Co-precipitation

Figure 7:
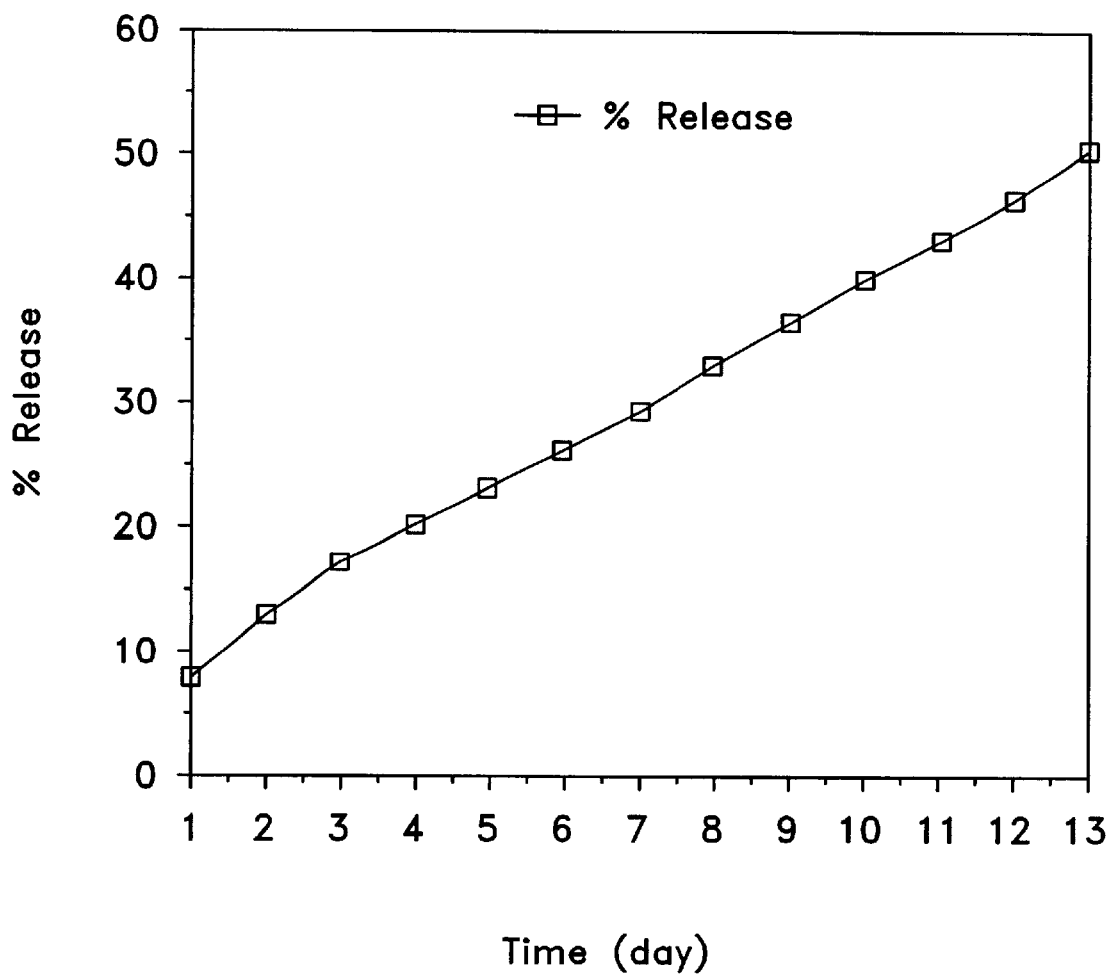

20% solutions of trehalose, lactitol, palatinit, GPM or GPS, containing MWPB and protein (phycoerythrin) were dried by spraying into an acetone-solid carbon dioxide freezing bath. The precipitated powders were separated by centrifugation or filtration and air dried to remove residual solvent. The powders again showed a monodisperse particle distribution and those containing buffer formulation salts remained dry at ambient temperatures and humidities.

e) Formation of Composite Vitreous Solid Dose Delivery Vehicle of Hydrophobic Active in SP by Drying from Organic Solvents Two different solvent systems were used to produce composite glasses. In the first case, CSA was dissolved in absolute ethanol and an equal volume of water was then added slowly so that the CSA which precipitated on each addition was allowed to redissolve. Trehalose was then dissolved in the 50% v/v ethanol solution to a final concentration of 50% w/v. Composite glasses were produced by evaporating the mixed solvent on a hotplate at 70° C. In the second case, CSA and trehalose were both dissolved in DMF and again the composite glass was made by evaporation as described above. In both cases, a slightly opalescent glass resulted. Drops of water were then overlaid on the glass films to study the dissolution and release properties of the glasses.

The results obtained indicate that the glasses behaved remarkably differently. Glasses made from DMF were water repellent with an obviously hydrophobic surface. They gradually developed opaque white patches and clumps of precipitated CSA where they were in contact with water. Glasses made from 50% ethanol were hydrophilic. They dissolved rapidly in the water and in doing so they released a cloud of very fine CSA particles. This latter glass appeared to contain CSA in either a fine solid suspension or a solid solution in the trehalose glass which released the CSA as a precipitate when the trehalose dissolved. As such, it represents a very useful dosage form for CSA with high bioavailability due to its uniform and finely divided format after release.

The different behavior of glasses of identical composition after drying from different solvents suggests an interesting and useful process providing precise control over the pattern of deposition of the different glasses during solvent evaporation. Since CSA is more soluble in DMF than is trehalose, composite glasses of 10–20% CSA in trehalose prepared from this solvent tend to have hydrophilic trehalose cores and hydrophobic CSA coatings. In contrast, when 50% ethanol evaporates, the early loss of ethanol in the 97% azeotrope causes CSA to come out of solution surrounded by trehalose syrup which then solidifies as the continuous phase leading to a CSA in trehalose glass solid emulsion.

EXAMPLE 3

Protection of Proteins Against an Organic Solvent and Elevated Temperatures Effected by Drying in Trehalose a) Protection of Horseradish Peroxidase and Alkaline Phosohatase Against Acetone Effected by Drying in Trehalose A 0.1 mg/ml horseradish peroxidase solution or a 1 mg/ml alkaline phosphatase/4 mg/ml bovine serum albumin solution was dried in an FTS Systems freeze drier with or without 50% trehalose. The drier was used as a vacuum drier and the mixtures dried without freezing. Four times the volume of solvent was added and the solution was allowed to evaporate to dryness. The contents were redissolved in 5 milliliters of water, and enzyme activity was assessed, in serial dilution, by commercial 'kit' reagents. The alkaline phosphatase kit was obtained from Sigma Chemical Co. and the horseradish peroxidase kit was obtained from Kirkegaard & Perry Laboratories, Inc. As shown in FIGS. 5A and 5B, the enzymes dried with trehalose were more resistant to acetone than the enzymes dried without trehalose.

b) Protection of Phycoerythrin Against Organic Solvents Afforded by Drying in Trehalose A 400 μg/ml phycoerythrin solution was freeze-dried in a Labconco freeze-drier with or without 20% trehalose. The dried protein powder was exposed to a number of organic solvents for 72 hrs. The phycoerythrin remained fluorescent in acetone, acetonitrile chloroform and methanol. In pyridine, the phycoerythrin remained fluorescent for 24–48 hr but began wetting and lost fluorescence by 72 hrs. In dimethylsulfoxide, the powder solubilized but the phycoerythrin remained fluorescent.

c) Protection of Phycoerythrin Against 100° C. Afforded by Drying in Trehalose

A 400 μg/ml phycoerythrin solution was freeze-dried in the FTS drier with or without 20% trehalose. The dried protein was stored at 100° for one month with no loss of functional activity.

EXAMPLE 4

Preparation of Vitreous Solid Dose Delivery System with Guest Substance Incorporated in Composite SP and/or HDC and/or Carboxylate Glass a) Coformulation of Vitreous Solid Dose Delivery System of Composite SP and Organic Glasses by Evaporation Microparticles of trehalose containing MB9 were prepared by spray drying as described in Example 2b. The solution dried contained 0.39 M trehalose and 0.14 M calcium lactate and 0.5% MB9. These particles were coated by adding them to a saturated solution of zinc palmitate ($ZnC_{16}$) in toluene and cooling from 60° C. to 30° C. This deposited a layer of $ZnC_{16}$ on the particles which were then filtered under vacuum to remove the excess $ZnC_{16}$, washed with acetone and air-dried. The resulting powder remained unwetted in water for at least three days (the particles floated in the water without sinking or releasing MB9 and thereafter slowly released dye into the water). Thus, otherwise water soluble powders may be made water impermeable by coating with metal carboxylates such as $ZnC_{16}$ to yield slow release formats. Note that the coating material is most likely in crystalline form and not a glass; therefore, the solid phase in which the guest substances are suspended need not be in the glass phase to be water impermeable.

b) Coformulation of Vitreous Solid Dose Delivery System of SP Glasses Containing Active and Organic Glasses By Evaporation A powdered trehalose glass containing phycoerythrin was added to a mixed carboxylate glass, namely a 1:1 mixture of sodium octanoate and zinc ethylhexanoate, dissolved in an excess of chloroform and evaporated under a stream of $N_2$ at room temperature to yield a carboxylate glass containing phycoerythrin powder in solid suspension or solution. The coformulated glass remained insoluble in water for at least 48 hrs. The phycoerythrin powder remained fluorescent both in the initial organic solution and in the final glass.

c) Coformulation of Vitreous Solid Dose Delivery System of SP Glasses Containing Active and Organic Glasses by Co-melting A preformed organic glass formed by quenching a melt of 1:1 mixture of sodium octanoate and zinc ethylhexanoate was softened at 95° C. and a powdered trehalose glass containing phycoerythrin was added to the melt. The resultant mixture was immediately quenched on an aluminum block precooled to 15° C. A clear carboxylate glass formed containing encapsulated phycoerythrin powder which retained its biological functionality as assayed by its ability to fluoresce. Varying the nature and ratios of the carbohydrate and organic moieties in the coformulated glasses results in glasses with a range of slow-release characteristics as assessed from their variable dissolution times in water.
d) Coformulation of Vitreous Solid Dose Delivery System of SP Glasses Containing Active and HDC Glasses by Evaporation The delivery systems were prepared by spray drying using a Buchi B-191 spray drier. Preformulated spray-dried trehalose/MB9 dye (1%) 6 µm particles (0.264 g) were suspended in a solution of TOAC (4 g) and azobenzene (0.029 g) in dichloromethane (100 ml) and spray drier at an inlet temperature of 40° C. A muddy yellow, hydrophobic powder was obtained with the TOAC glass, incorporating the yellow dye azobenzene, encapsulating the trehalose glass incorporating the blue dye MB9. The composite delivery vehicle showed delayed release of the intense, water soluble blue dye MB9 when immersed in an aqueous solution.
e) Coformulation of Vitreous Solid Dose Delivery System of SP Glasses Containing Active and Plastics by Evaporation A powdered trehalose glass containing phycoerythrin prepared according to Example 1 was added to a solution of perspex dissolved in an excess of chloroform and evaporated under a stream of $N_2$ at room temperature to yield a solid perspex block containing the phycoerythrin powder in solid solution. The phycoerythrin powder remained fluorescent both in the initial organic solution and in the reformed solid perspex which was impermeable to water even after 4 weeks. Similar results were obtained with polyester dissolved in dichloromethane and polyurethane dissolved in dimethylsulfoxide.

EXAMPLE 5

Preparation of Hollow Needles Filled with Delivery Systems

The end of a billet of a trehalose glass tubes with a central cavity filled with a powdered trehalose glass containing phycoerythrin prepared according to Example 1 was melted in a zone furnace and the fiber drawn by winding onto a metal drum rotated at constant speed. The hollow fibers formed contain the finely powdered trehalose-stabilized compound and can be cut to any desired size. The hollow fiber can also be made of biodegradable thermoplastic or organic or HDC and by varying the diameter of the fibers produced, the filled needles can be formed which vary from micro to macro needles, i.e. from thicknesses of microns to fractions of a millimeter. The hollow needles may be filled with any solid dose vehicle described herein.

EXAMPLE 6

Ballistic Delivery of Solid Dosage Delivery Systems

Powdered glasses were injected into the skin by propulsion at hypersonic speeds using a pressure shock wave created by the release of compressed gas. The powder was held in the chamber attached to the large end of a funnel-shaped cavity to the smaller end of which was attached a cartridge of compressed gas sealed by a mylar film and the hypersonic shock wave was generated by rupture of the mylar membrane. Alternatively, a timer relay-driven solenoid can be used to control the helium release which would allow functioning at lower helium pressures. This is the principle used in the particle inflow gun (PIG) developed by Finer for transforming plant tissues. Vain et al. (1993) *Plant Cell Tissue and Organ Culture* 33:237–246.

EXAMPLE 7

Preparation of Solid Dose Delivery Systems of Organic Glasses by Evaporation a) Preparation of Carboxylate Solid Dose Delivery Systems by Solvent Evaporation Aluminum hexanoate was dissolved in chloroform (0.5 g/10 ml) together with a fine suspension of 1 wt % MB9 as a tracer dye. A fine amorphous film (100–200 μm thickness) was formed by casting on silicate glass slides and evaporating off the solvent in a warm air-stream. Release of dye into distilled water was monitored over 5 hr and is shown in FIG. 6. No devitrification of these glasses was observed and the films remained transparent, though they decolourised as the dye diffused out into medium.

Amorphous films were also formed from calcium neodecanoate dissolved in chloroform (0.5 g/10 ml) as described above. Release of dye from these thicker (1–2 nm thickness) films into distilled water was again monitored over 24 hr and is shown in FIG. 6. In contrast to the Aluminum films, dye release from the calcium neodecanoate films followed the dissolution of the films as monitored by atomic adsorption spectroscopy of $Ca^{2+}$.

b) Preparation of Composite Vitreous Solid Dose Delivery Systems of SP Glass Containing Active Incorporated into Carboxylate Glass by Evaporation Films of glucose glass incorporating 1 wt % MB9 were formulated by quenching from the melt. These films were coated with thin (100 μm thickness) amorphous metal carboxylate films by evaporation of solution of the carboxylate in chloroform (0.5 g/10 ml). The metal carboxylates used were aluminum hexanoate and octanoate, calcium neodecanoate and magnesium isostearate and neodecanoate. Dissolution of the films was monitored by release of dye into distilled water. These delivery systems delayed dye release for times ranging from minutes to hours, except for those formed from magnesium isostearate which delayed release of dye for 10 days.

EXAMPLE 8

Preparation of HDC Solid Dose Systems

Several HDC glasses were prepared by melting and quenching. In the following Examples, the component HDCs were purchased from Aldrich Chemicals with the exception of TOPR which was synthesized according to the method described by Akoh et al. (1987). The components formed glasses with little if any decomposition. The fructose, sucrose and to some extent, glucose, melt with noticeable decomposition or polymerization. An ester such as α-D-glucose pentaacetate is stable at its melting point and forms a clear colorless glass as it is being quenched. The greater stability of the ether and ester derivatives is clearly an advantage in the encapsulation of reactive organic materials such as pesticides and biocides.

The HDCs with particularly low melting points form soft waxy glasses after being quenched. The nmr spectrum of vitreous α-D-glucose pentaacetate was found to be identical to that of the crystallized α-D-glucose pentaacetate.

The glass formed from β-D-glucose pentaacetate is poorly soluble in water and a disc (20 mm diameter and 2.5 mm thick) prepared from this ester placed in flowing water lost about 33% of its original weight in 10 days. Another glass disc of similar dimensions was prepared from α-D-glucose pentaacetate and placed in 1 l of water, which was replaced daily. After 7 days, the glass had lost 20% of its original weight. The rate of release of encapsulated Acid Blue dye from this glass, as shown in FIG. 7, was quite constant. The release rate of the dye was higher in the first day as the release happened mainly from the surface of the glass disc.

Excellent recoveries were obtained in the encapsulation of several organic substances in the glasses. Glass discs of α-D-Glucose pentaacetate containing 2% w/w of the materials listed in Table 4 were formed by melting and quenching and then ground. Photochrome II is 5-chloro-1,3-dihydro-1,3,3-trimethyl spiro[2H-indole-2,3'-[3H]-napth[2,1-b][1,4]-oxazine. The encapsulated materials were extracted by the suitable solvent such as methanol or water. The results obtained are depicted in Table 4.

TABLE 4

| Encapsulated material | b.p. ° C. | m.p.° C. | Application |
| --- | --- | --- | --- |
| Acid yellow 65 | | >300 | Water soluble dye |
| Acid blue 129 | | >300 | Water soluble dye |
| Disperse red 1 | | 161 | Non-linear optical material |
| Mordant blue 9 | | >300 | Water soluble dye |
| Ethyl hexanoate | 168 | | |
| Ethyl octanoate | 207 | | |
| Oxadiazon | | 90 | Pesticide |
| Azobenzene | 293 | | |
| Melatonin | | 117 | veterinary hormone |
| Photochrome II | | 183 | Photochrome |

The rates of release of Acid Blue 129 were found to depend on the dissolution rates and shapes of the glasses. Pesticide-like Oxadiazon was dissolved easily in the melt of this glass at about 15% w/w without problem.

EXAMPLE 9

Formation and Release Properties of Vitreous HDC Solid Dose Delivery Systems by Quenching from the Melt a) Formation and Release Properties of Simple and Composite Vitreous HDC Glasses from the Melt In the following experiments, the delivery system was preformulated, whether as a single material, or as a mixed composition. This was carried out by intimately grinding the component HDCs together, followed by careful, controlled melting in a furnace, between 120–140° C. and with normal atmosphere to form melts. The melts were quenched to glass by pouring over a brass block. This glass was then finely ground.

MB9 dye (1 or 5 wt %) was mixed with the ground glass prior to re-melting at 140° C. The melt was quenched to form small glass beads (2.5 mm diameter) which were used in controlled release experiments.

Controlled release of encapsulated dye was monitored by suspending three such beads in 25 or 50 ml of deionized water or PBS solution at ambient temperatures (27–30° C.) or at 37° C., as indicated. The media were undisturbed, except for periodic stirring and were replaced at set intervals with fresh media (generally at 72 hr intervals). Both single HDC glasses and composite HDC glasses were formed. The HDC composite glasses formulated are shown in Table 5. Dye release was measured by Spectrophotometry (516 nm λmax) and the results are presented in FIGS. 8–14. The TOAC glass shows zero-order release characteristics. The use of other HDCs as glass modifiers in the composite HDC formulations enable the tailoring of the glasses formed to yield the release characteristics desired.

TABLE 5

| Glass System | Wt % MB9 | Temp/° C. | % Ratios |
| --- | --- | --- | --- |
| 1. TOAC | 1 and 5 | RT, 37 | 100 |
| 2. RUDA | 1 and 5 | RT | 100 |
| 3. TOAC/SOAC | 1 | RT | 75 (wt) |
| 4. TOAC/αGPAC | 1 | RT, 37 | 75 (wt) |
| 5. TOAC/COAC | 1 | RT | 75 (wt) |
| 6. TOAC/TOPR | 1 | RT | 75 (wt) |
| 7. TOAC/βGPAC | 1 | RT | 75 (wt) |
| 8. TOAC/αGPAC | 1 | RT | 90, 75, 50, 25, (mole %) |
| 9. TOAC/RUDA | 1 | RT | 90, 75, 50, 25, (mole %) |

Figure 8:
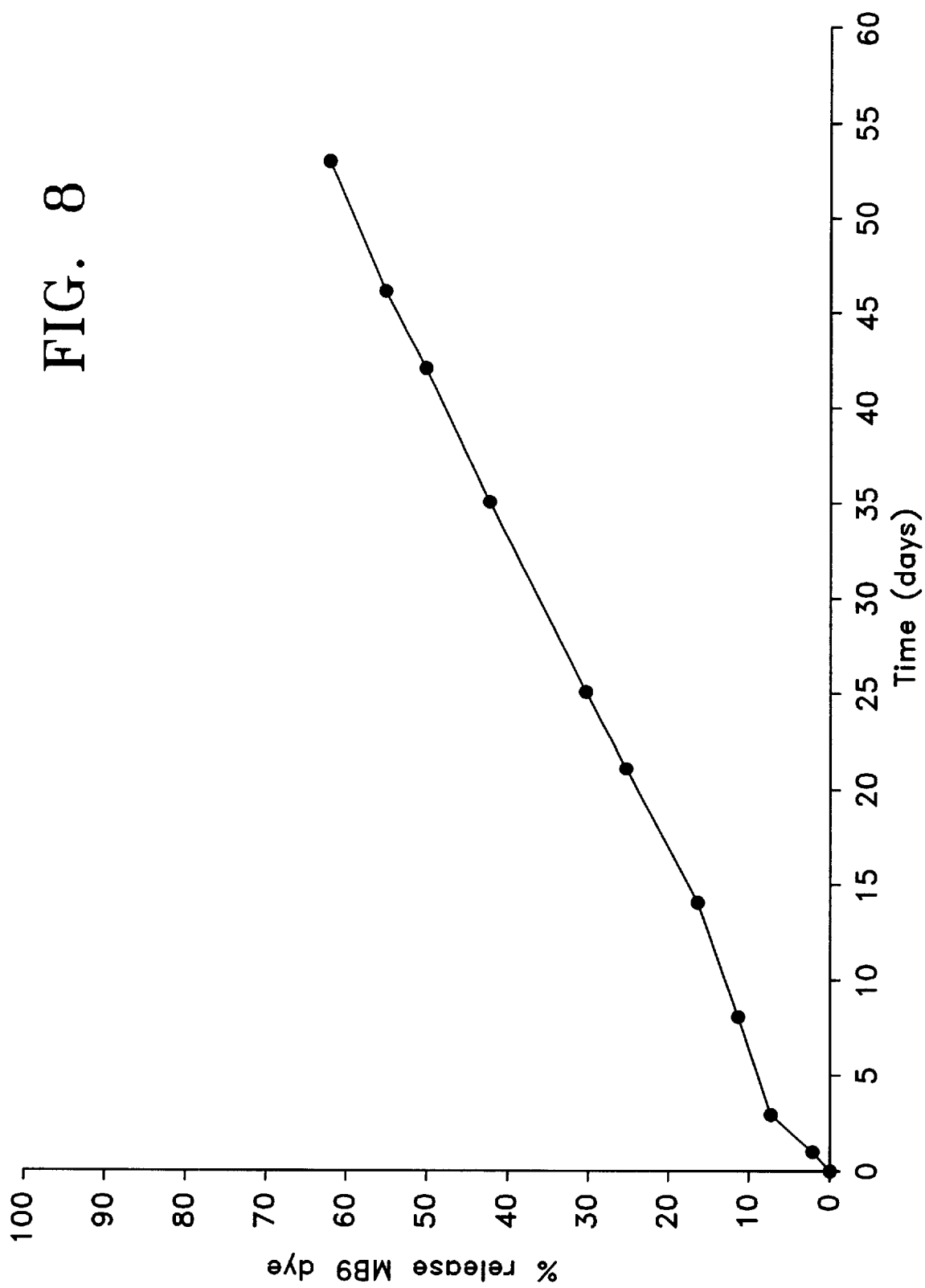

FIG. 8 depicts the zero-order release characteristics of TOAC delivery systems. In FIG. 8, the results were obtained from TOAC glass discs (6 mm×2.5 mm) with MB9 dye evenly dispersed therein at 2 wt %. Release was controlled at 25° C. with gentle stirring and media changes at regular intervals. Note the linear release of MB9 dye over a 55 day period. The results presented in FIG. 8 indicate that a pure HDC vitreous delivery vehicle system gives zero-order release rates of guest substances. The results presented in FIGS. 9–14 show variation on release rates by changing the ratios of different HDCs in the delivery systems, changing the carbohydrate backbone length and by changing the nature of the derivative on the carbohydrate backbone. In each instance it is clear that the HDC delivery systems allow a wide range of release rates that can be tailored to the guest substance and the delivery thereof.

Figure 9:
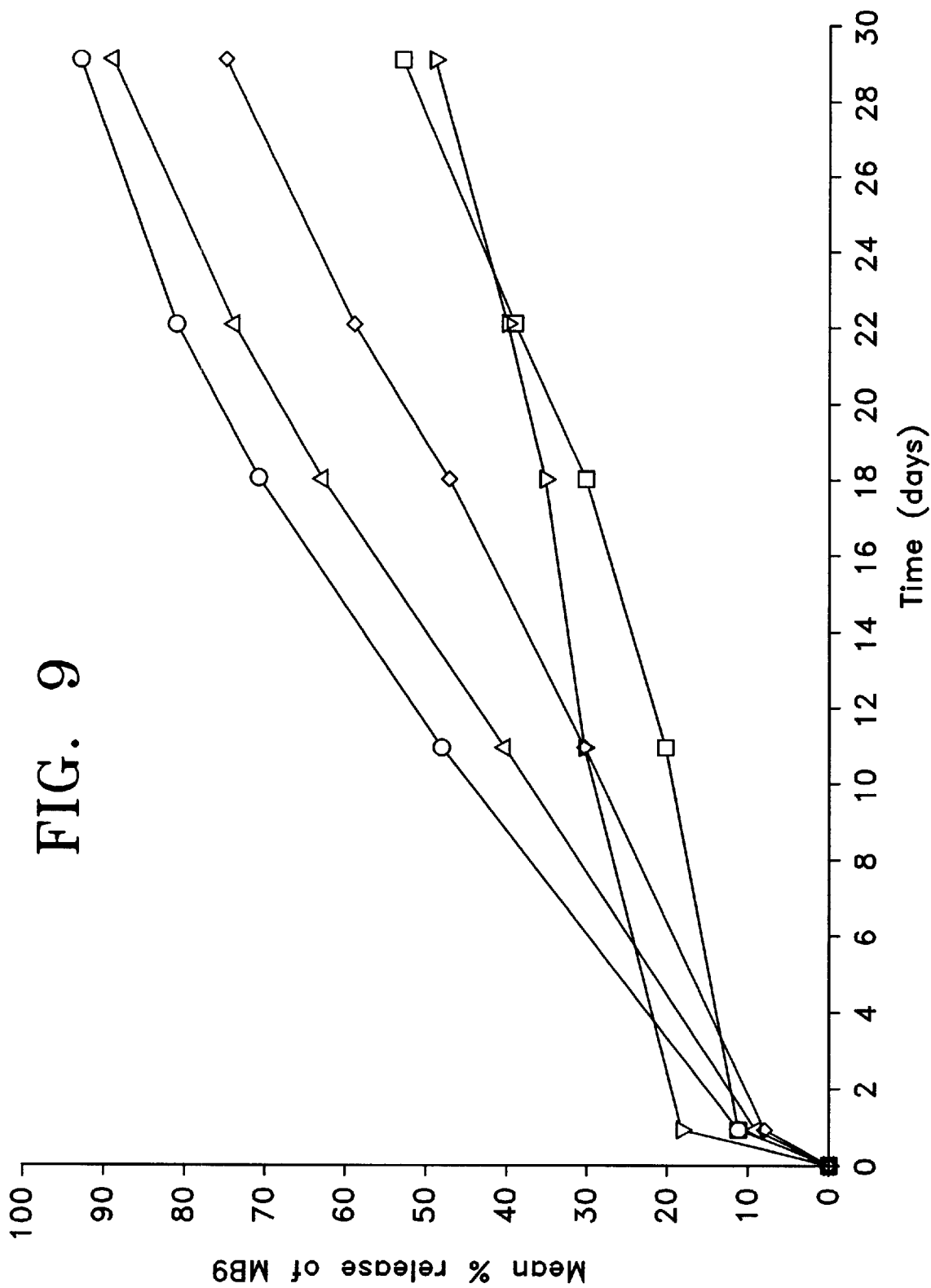

FIG. 9 depicts the results obtained when the ratios of two different HDCs vary in the delivery system. The rate of release of MB9 was measured from TOAC/RUDA matrices as described for FIG. 8. The rate of release was seen to vary with the different formulations but was not directly related to the concentration of RUDA. For instance, the highest rate of release was seen with 75% TOAC (25% RUDA) and the lowest rate of release with 95% TOAC. Thus, the rate of these delivery systems may be readily, empirically derived.

Figure 10:
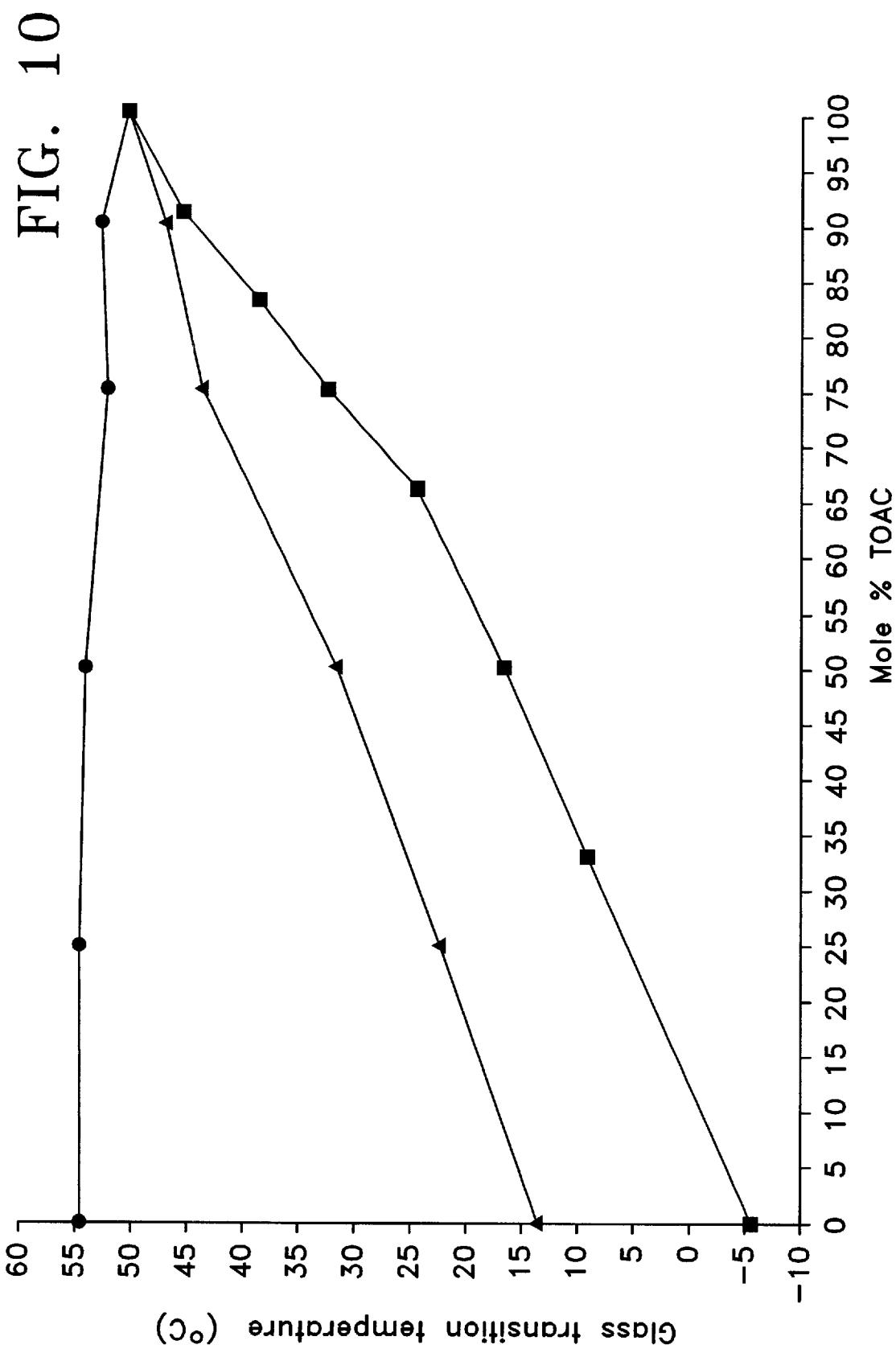

FIG. 10 compares the change in Tg of three different coformulations of HDCs with varying amounts of TOAC. Three different coformulations were tested, TOAC/SHAC, TOAC/RUDA and TOAC/α-GPAC with increasing mole % of TOAC. These results indicate that the Tg of the vehicles increases directly with the mole percentage of TOAC in those coformulations which originally had a lower Tg TOAC/α-GPAC and TOAC/SHAC.

Figure 11:
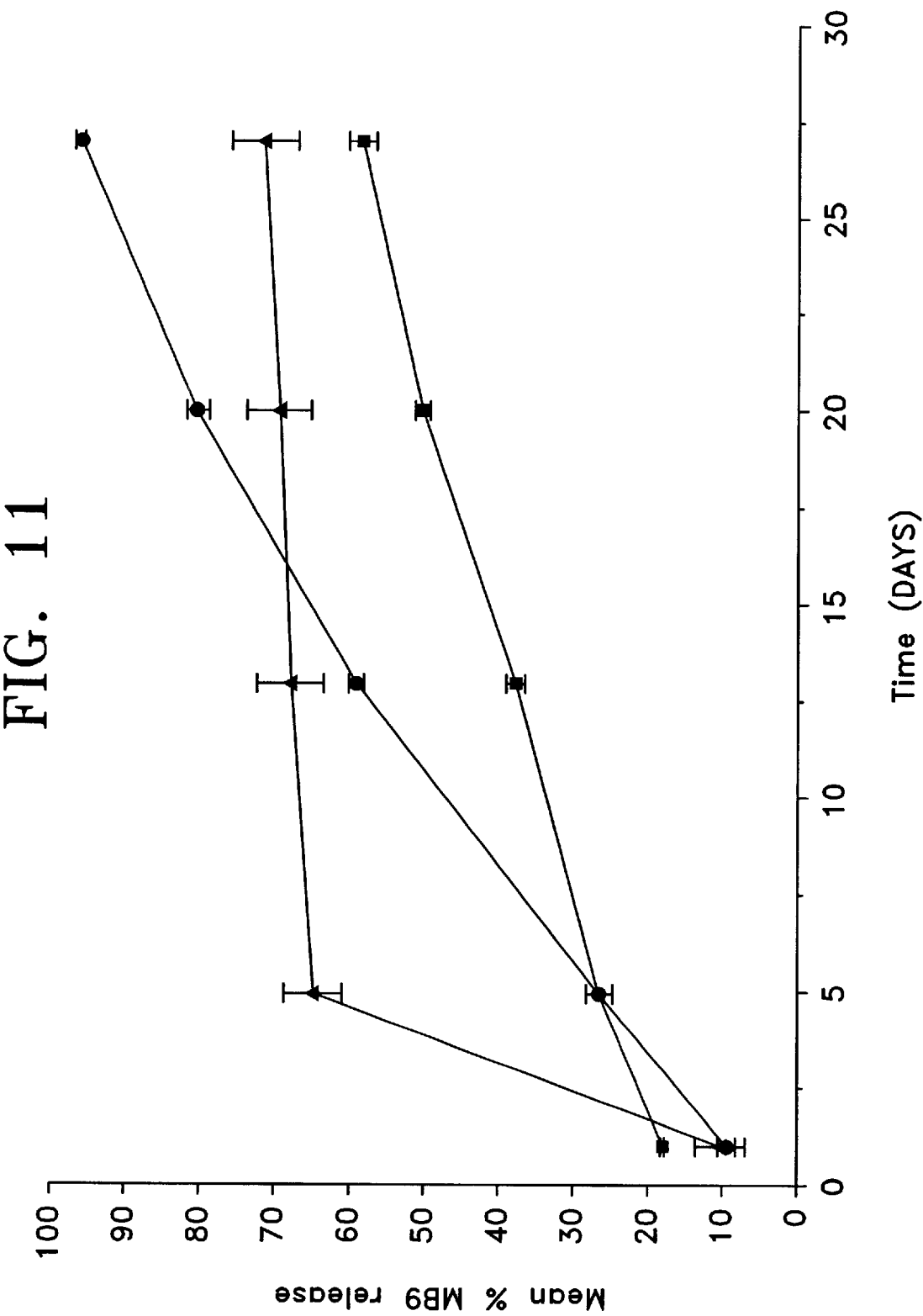

FIG. 11 compares the percent release of MB9 dye from two different coformulations of TOAC/RUDA and RUDA alone. RUDA has a biphasic release rate with an initial fast release of about 60% of the dye in 5 days and a slow release of a few more percentages of the dye over the next 25 days. The release rate of RUDA alone is substantially modified by the presence of TOAC. The formulation of 50% RUDA shows a near linear release rate greater than that of the 10% RUDA formulation.

Figure 12:
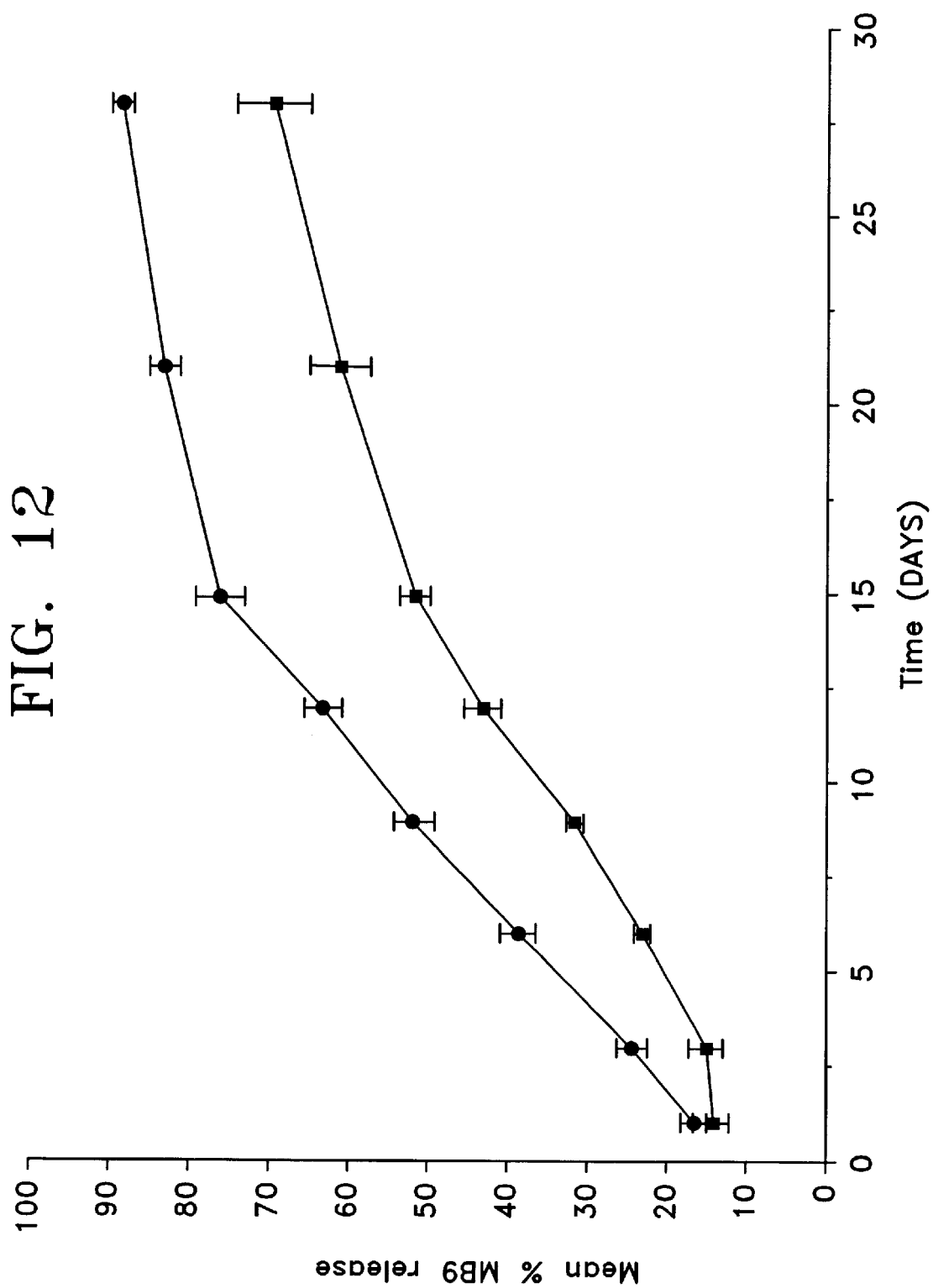

FIG. 12 compares the release of MB9 dye from coformulations of TOAC (75%) with either SOAC or COAC to show the effect of varying the carbohydrate backbone. The results show that release rates can be varied in this manner, the TOAC/COAC coformulation showed an increased release rate compared to the TOAC/COAC coformulation.

Figure 13:
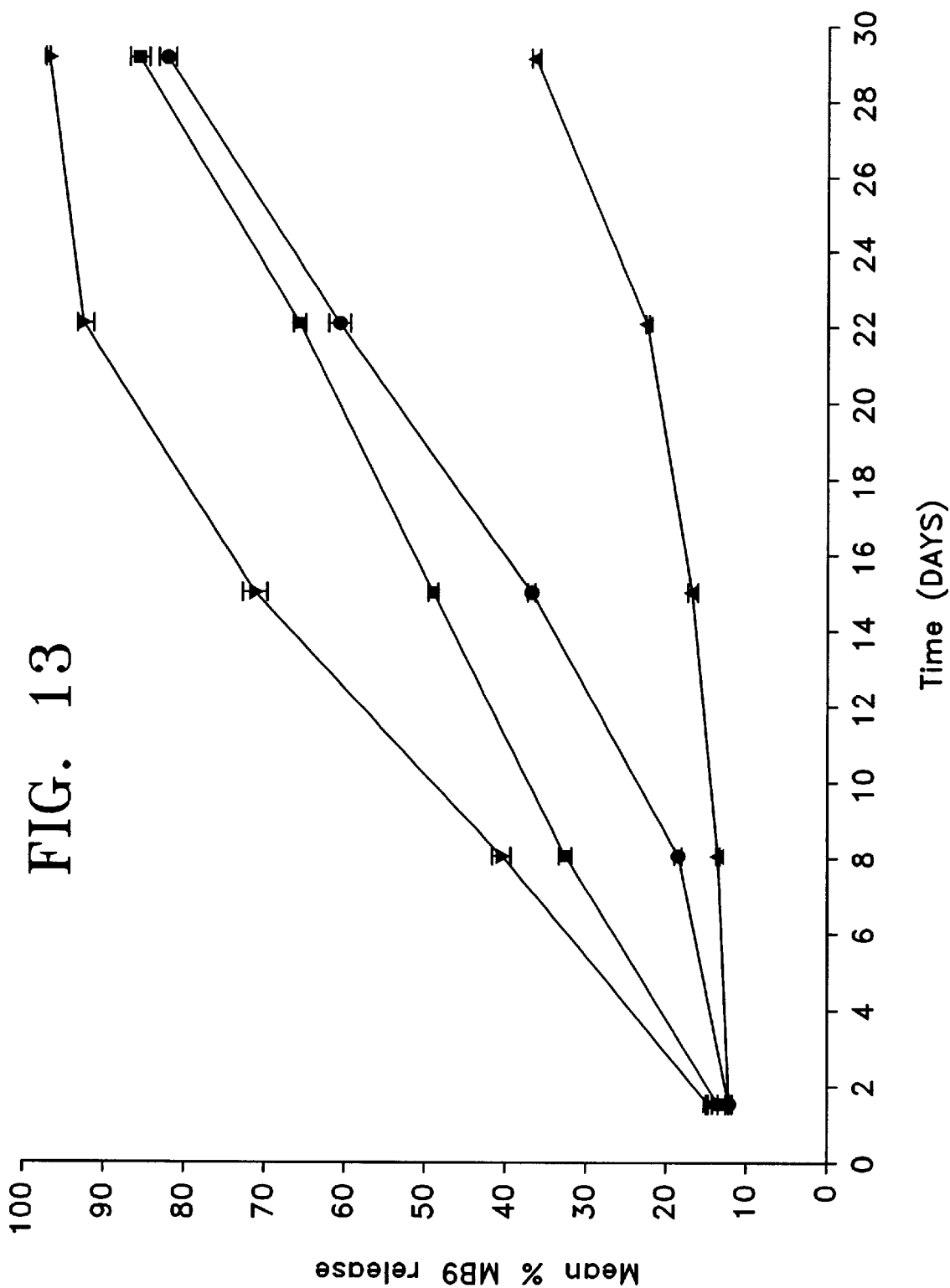

FIG. 13 compares the release rate of MB9 dye from coformulations of two HDC components of different carbohydrate backbone length, TOAC and α-GPAC. The release rates were not directly related to the weight percent of TOAC with 50% TOAC having the lowest release rates and 25% having the highest. Again, the rates are readily determined empirically.

Figure 14:
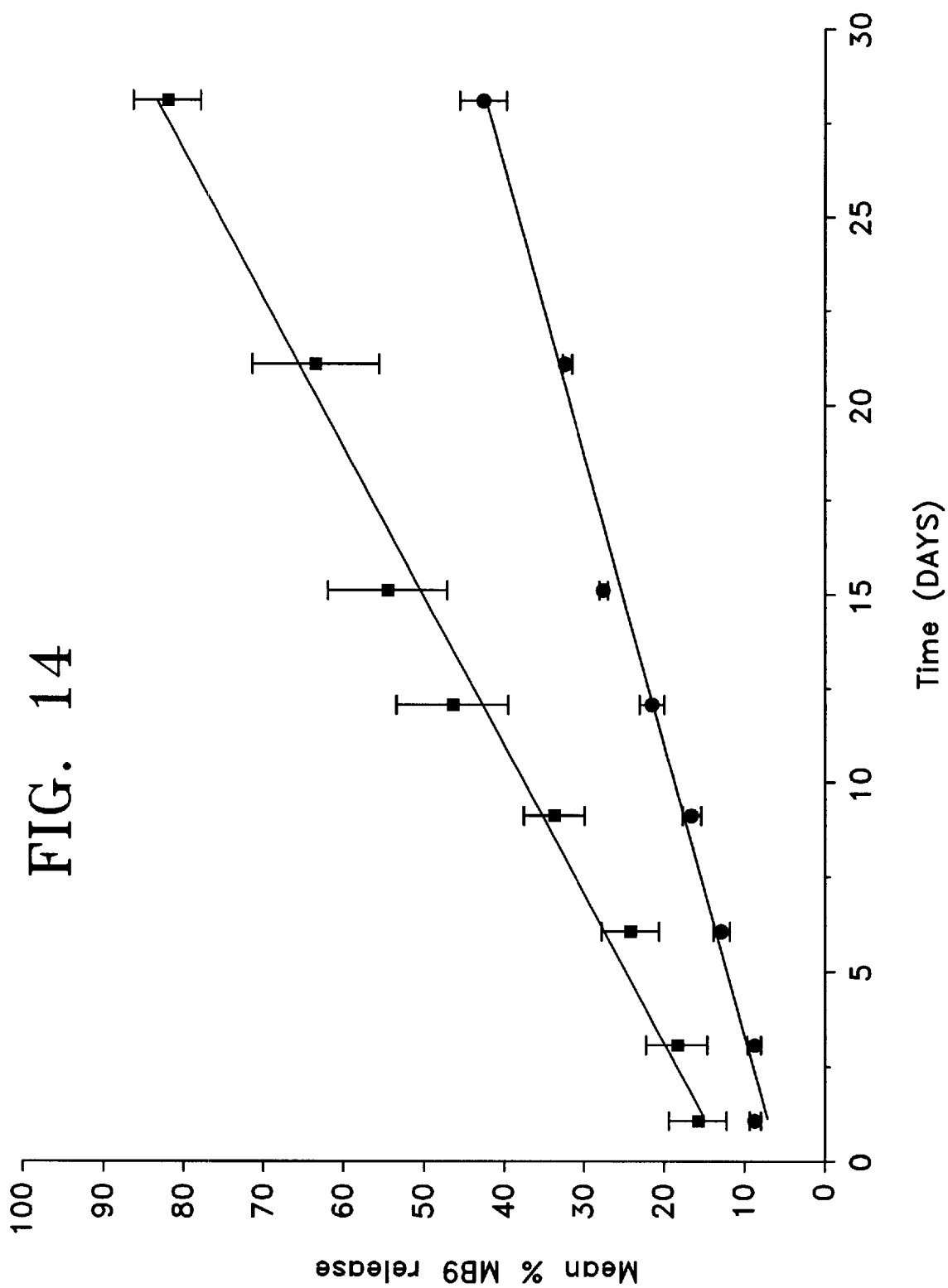
FIG. 14 is a graph depicting MB9 release from TOAC (■) and TOAC/TOPR (25 wt %) (●) (n=5).

FIG. 14 compares the release rate of MB9 dye from two different coformulations of HDC components with the same carbohydrate backbone and different derivatives, TOAC and TOPR. The results indicate that adding 25% TOPR to a TOAC delivery system dramatically decreases the release rate of the guest substance.

b) Incorporation of Guest Substances in HDC by Quenching from the Melt

Dissolution of synthetic corticosteroid XPDO (described below) into a TOAC melt and quenching to form the vitreous solid dose delivery system was achieved. By looking at the release of MB9 into aqueous solution, these experiments tested the compatibility of the steroid within the glass, subsequent recovery of the steroid and studied the effect that XPDO has on the properties of the delivery system formed looking at the release of MB9 into aqueous solution. TOAC (3.21 g) was pre-melted at 150° C., before being quenched to glass. The glass was finely ground with XPDO (0.15 g) before being remelted. The clear melt was again quenched to yield the composite HDC/active glass. Thermal analysis was carried out on a Rheometric Scientific Differential Scanning Calorimeter (DSC) at a heating rate of 10°/min under a nitrogen atmosphere. The following samples were prepared:

| | |
|---|---|
| 1. TOAC/XPDO (5 wt %). | Tg = 50.6° C. |
| 2. TOAC/XPDO (5 wt %) + MB9(1 wt %). | Tg = 50.9° C. |
| 3. TOAC alone. | Tg = 50.1° C. |
| 4. TOAC/MB9 (2 wt %). | Tg = 50.3° C. |

Figure 15:
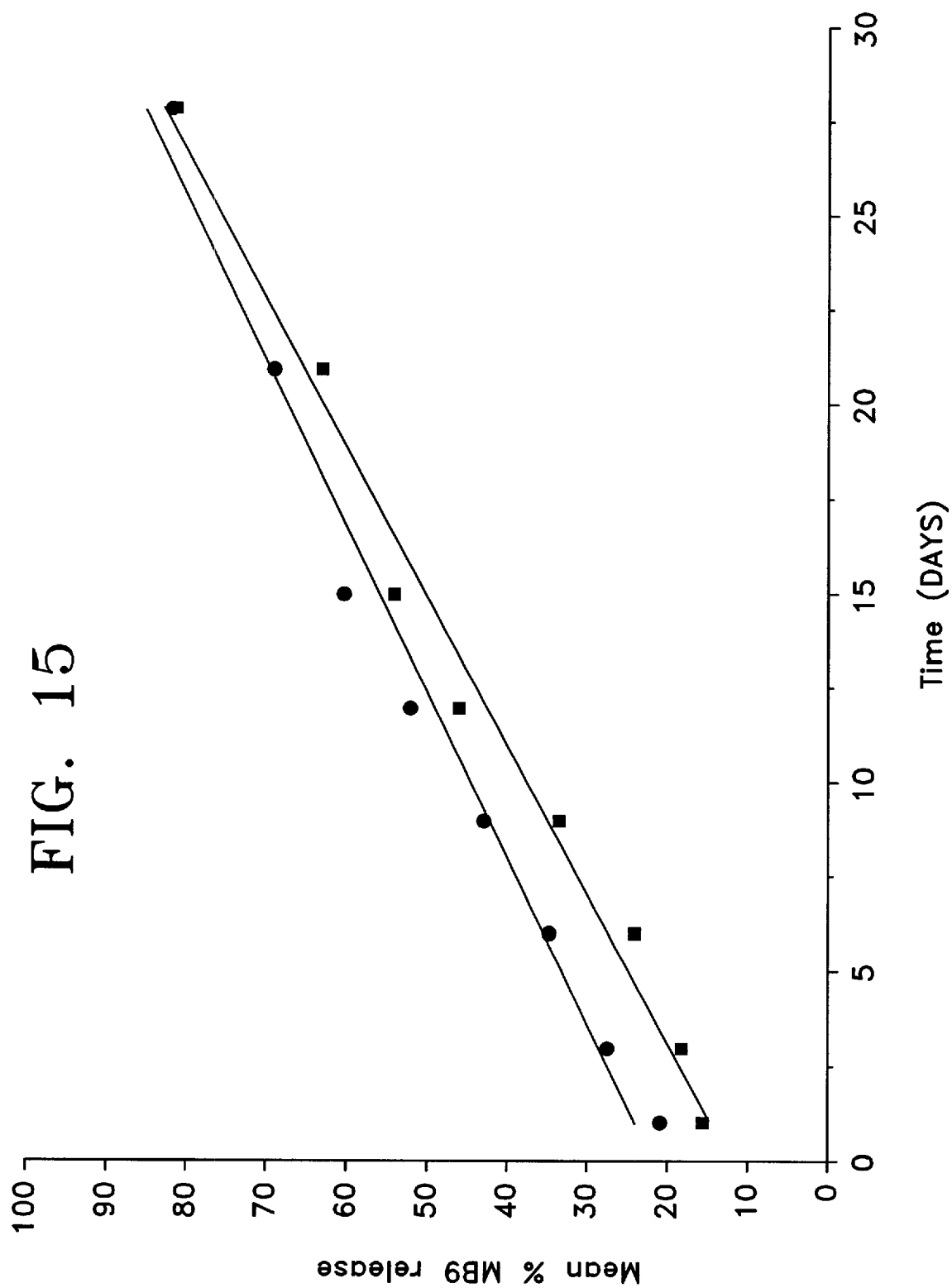
FIG. 15 is a graph depicting MB9 (1 wt %) release from TOAC alone (■) and TOAC plus XPDO (5%) (●) (n=5).

Release characteristics of the vitreous HDC solid dose delivery systems were studied by monitoring the release of MB9 from TOAC/XPDO glasses as shown in FIG. 15. For analysis of stability of active in the vitreous HDC solid dose delivery systems, XPDO was recovered from the samples by dissolving the glass in acetonitrile and analyzing by HPLC. There was full recovery of the guest substance even after storage at 45° C. for 4 weeks.

EXAMPLE 10

Formation of Vitreous HDC Solid Dose Delivery Systems by Evaporation of Solvent a) Formation of HDC Glasses by Solvent Evaporation As described above, it was found that TOAC makes a good delivery vehicle by quenching from the melt. Such a delivery system has a low melting point and very little tendency to recrystallize. A series of experiments were then performed on TOAC glasses made by solvent evaporation on 3×1" soda-glass slides.

Dichloromethane (DCM) and chloroform are standard solvents for TOAC, which is also soluble in other solvents such as acetonitrile. DCM was used for all subsequent experiments.

Glasses were made by evaporating DCM on a hotplate set at 65° C. from a 25% solutions of TOAC (50% solutions often deposited crystals in the pipette tip). Drying was carried out for 2 hr to be certain of complete dryness.

Uniform glasses were produced by using an Eppendorf-type pipette to deliver 100 μl to a slide recently placed on the hotplate and then removing about 50 μl by using the clear/expel volume of the pipette. Glasses were very clear and adherent when first made but gradually recrystallized over 1 month at room temperature (RT) and 50–60% relative humidity (RRH).

Trehalose glasses similarly made by evaporating water from a 50% trehalose solution were clear when first formed but gradually recrystallized over a period of several weeks.

b) Incorporation of Active into HDC Glasses by Solvent Evaporation: Powders Suitable for By-inhalation XPDO is a steroidal anti-inflammatory compound. Chemically it is 6α,9α-difluoro-11β,21-dihydroxy-16α,17α-propyl methylene dioxy-4-pregnene-3,20-dione. XPDO crystallizes as helices which pack together in needles to leave long intermolecular void spaces which bind water molecules in a manner reminiscent of zeolites. This makes the steroid sufficiently hygroscopic to preclude its use in a dry powder inhaler, which is its preferred method of administration. In the amorphous (non-crystalline) form, XPDO is non-hygroscopic but is chemically unstable. Studies on stabilizing this compound with trehalose were unsuccessful as it was not possible to produce a non-hygroscopic powder.

XPDO was therefore incorporated into a TOAC glass by dissolving both crystalline TOAC and XPDO in DCM and evaporating the solvent at 70° C. on a hotplate. XPDO was used in proportions of 10% and 20% of total solids in the final TOAC glass. These glasses were perfectly water clear and transparent. When stored at RH of 75%, 81%, 90% and 95% for 4 weeks they showed no change in glass structure such as recrystallization.

However, when immersed in liquid water, the surface of the glass slowly recrystallized so that microscopic pyramidal crystals of TOAC could be seen under an inverted microscope within 15–30 min of addition of water. Crystallization was slowly progressive and within another few minutes small clusters of the typical needle shaped crystals of XPDO appeared. Since neither the needle shaped XPDO crystals nor the pyramidal TOAC crystals were adherent to the underlying glass, they were washed away readily to reveal a fresh glass surface for further slow dissolution. The complete exclusion of XPDO from the TOAC crystals ensured that this molecule, previously incorporated in the glassy TOAC matrix, was now released into the liquid phase.

c) Incorporation of Active into HDC Glasses by Solvent Evaporation; Spray Dried Powders Suitable for By-inhalation Studies were performed using the synthetic corticosteroid XPDO dissolved in DCM. The solution was spray dried in a Buchi B-191 spray drier, using an inlet temperature of 40° C. This resulted in an amorphous, fine, white powder, that contained XPDO in solid solution. XPDO was incorporated at 20 wt %. The powder was completely amorphous as confirmed by thermal analysis (Tg=46° C.).

For analysis XPDO was extracted from the spray-dried powder by dissolving the powder in acetonitrile and then diluting the acetonitrile with sodium phosphate buffer prior to analysis by HPLC. Samples were set up to test stability of XPDO in the spray dried formulations at 45° C. and stored over saturated Zinc sulphate (RH 80–85%).

For release into sodium phosphate buffer, 0.0868 g of the spray dried powder was shaken in 10 mls of the buffer for 1 minute. The suspension was then filtered through a 0.2 μm filter. On analysis by HPLC, it was concluded that the XPDO was effectively being released into aqueous solution. Bioavailability of the steroid from the delivery system was tested by immersion in an aqueous solution for a short time. Stability of the steroid in the spray-dried formulation was tested at high humidity and 45° C. (both factors are important if the application as an inhalable powder is to be successful). The results indicated a resistance to high humidity, stability in the glass and ready bioavailability in vitro tests. No evidence of any degradation was seen on HPLC analysis of the spray dried glass powder even after 4 weeks storage at 45° C. and 85% RH.

d) Incorporation of Guest Substances into HDC Glasses by Solvent Evaporation; Slow Release CSA Cyclosporine (CSA, Sandimmune©) is a hydrophobic cyclic peptide used as an immunosuppressive agent particularly in organ transplant patients. CSA is administered orally and intravenously. It is dissolved in alcohol for administration. In clinical practice, blood levels of this drug undergo severe fluctuations due to unreliable absorption from the proximal small bowel (jejunum). This problem could be overcome if CSA was released at a constant rate over several hours in a form suitable for absorption.

CSA was incorporated into a TOAC glass by dissolving both crystalline TOAC and CSA in DCM and evaporating the solvent at 70° C. on a hotplate. CSA was used in proportions of 5%, 10% and 20% of total solids in the final TOAC glass. These glasses were perfectly water clear and transparent. When stored at RH of 75%, 81%, 90% and 95% for 4 weeks they showed no change in glass structure such as recrystallization. When immersed in water, these glasses behaved similarly to the XPDO-containing glasses, i.e., they slowly re-crystallized as separate TOAC and CSA crystals.

e) Formation of Vitreous Solid Dose Delivery Vehicles of Composite HDC Glasses by Solvent Evaporation In addition to TOAC, two other hydrophobically modified saccharides, $\alpha$-GPAC and TOPR, have been studied in mixtures to provide mixed glasses with improved properties.

Mixed glasses of pairs of these HDCs were produced by mixing the crystalline components in various proportions and then producing glasses either by evaporation of the solvent DCM on a hotplate or by melting at 150° C. and quenching on a brass plate.

The resulting glasses were tested for their utility as controlled release matrices in two ways. First, they were assessed for their ability to resist devitrification on exposure to high RH at RT. Second, they were immersed in water or phosphate-buffered saline (PBS) to study their solubility and rate of erosion by surface recrystallization.

Single component glasses of both $\alpha$- and $\beta$-GPAC could only be made by quenching from the melt. When solvent evaporated, solutions of this HDC always crystallized. Single component glasses of TOAC and TOPR were readily produced by either solvent evaporation or quenching but were very susceptible to devitrification at high RH, showing complete recrystallization of thin glass films on microscope slides and surface recrystallization of quenched disks at RH from 75% to 95% after overnight exposure. The mixed glasses behaved as described in Table 6.

TABLE 6

| % GPAC | % TOAC | % TOPR | Initial Form | After RH 24 hr |
|---|---|---|---|---|
|  | 100 |  | Glass | Cryst + + + + |
| 10 | 90 |  | Glass | Glass |
|  | 90 | 10 | Glass | Glass |
| 50 | 50 |  | Glass | Glass |
| 90 | 10 |  | Cryst + + + + | ND |

TABLE 6-continued

| % GPAC | % TOAC | % TOPR | Initial Form | After RH 24 hr |
|---|---|---|---|---|
| 80 | 20 |  | Cryst + | Cryst + + + |
| 90 |  | 10 | Cryst + + + + | ND |

The results obtained indicate that the effect of different RHs was very uniform. While the pure TOAC and some of the composite glasses crystallized at all RHs from 75% to 95%, the other composite glasses remained amorphous at all the RHs studied.

The 10% $\alpha$-GPAC and 10% TOPR in TOAC glasses and the 50:50 molar ratio TOAC:$\alpha$-GPAC glass were also immersed in water to examine their rate of devitrification in liquid water rather than humid air. The first glass recrystallized within 20–30 min while the second developed a few small crystals after 4 hr while the 50:50 glass did not change over 4 days indicating surprisingly low solubility.

As a vehicle for powder delivery of drugs to the deep lung, the 10% $\alpha$-GPAC in TOAC glass shows the very desirable properties of resistance to 95% RH such as might be experienced in an inhaler and in the air passages with, at the same time, rapid recrystallization in liquid water such as in the fluid layer lining the alveolae.

Glasses of TOAC with or without the addition of 10% or more of $\alpha$-glucose pentaacetate or trehalose octapropanoate provide a range of resistance to ambient RH and of solubility rates allowing a degree of tailoring of the controlled release of drugs dispersed in such glasses.

f) Incorporation of Active into Composite, Slow Release HDC and/or SP Glasses by Solvent Evaporation For maximum utility, the slow release characteristics of HDCs should be usable with both hydrophobic and hydrophilic molecules. The former are readily prepared in solid solution in one of the HDCs either by solvent evaporation or by direct dissolution in the melt followed by quenching. Hydrophilic molecules are not directly soluble in HDCs.

Figure 16:
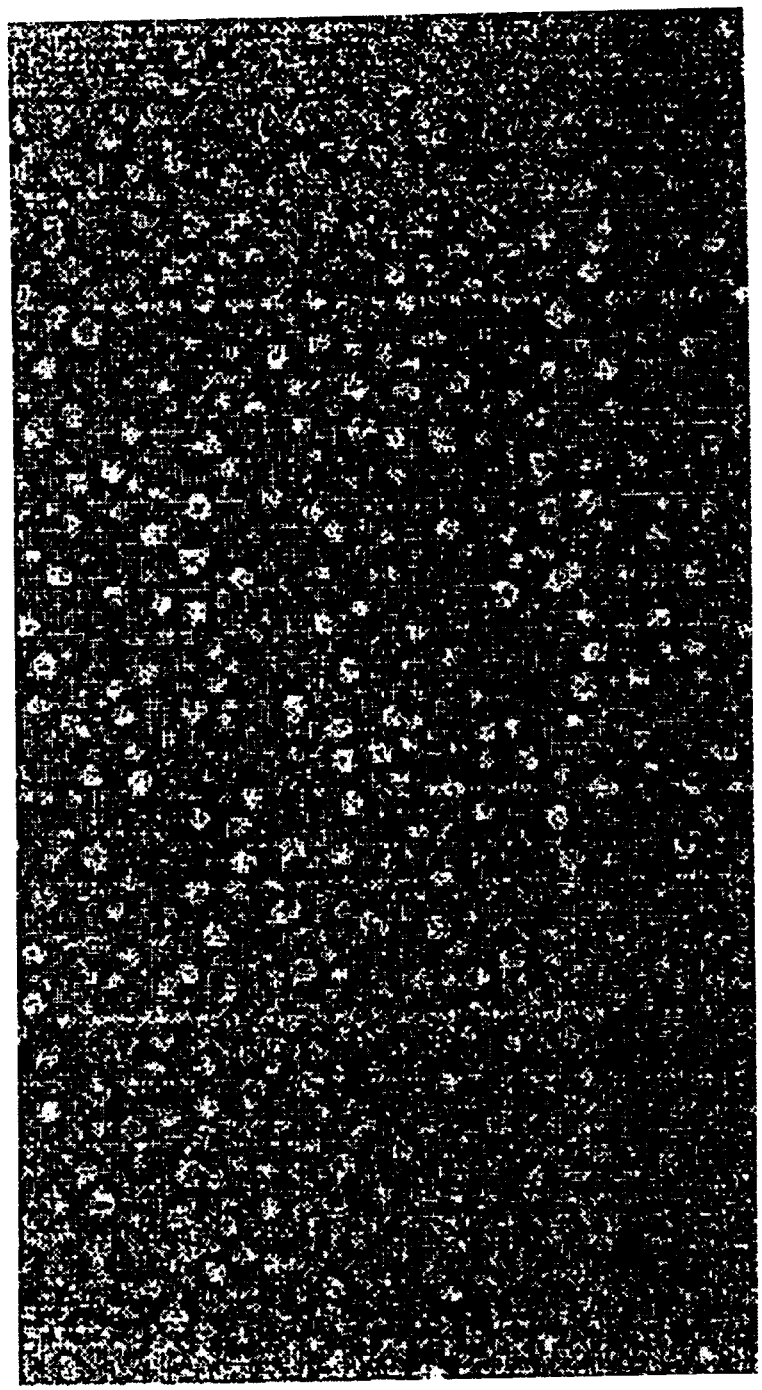
FIG. 16 is a photomicrograph of a thin film of a coformulation glass comprising 10% trehalose in TOAC dried from dimethylformamide (DMF).
Figure 17:
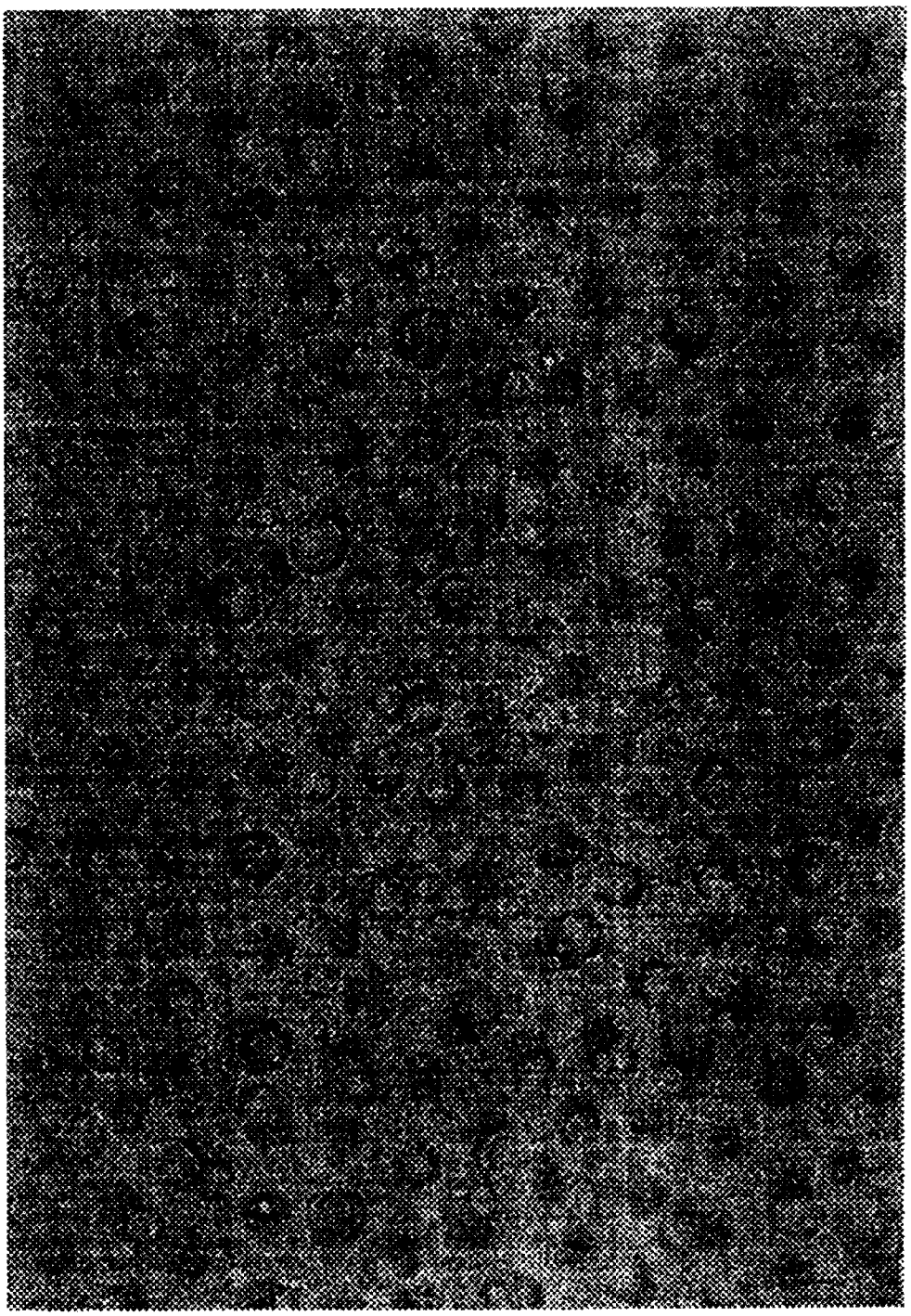
FIG. 17 is a photomicrograph of the coformulation of FIG. 16 at a higher magnification.

We have now found a remarkably useful method to incorporate hydrophilic substances in a very uniform and useful distribution in a matrix of HDCs. The process is well illustrated by using trehalose as the hydrophilic substance and TOAC as the hydrophobic matrix. Good solvents for both modified and native trehalose are DMF and DMSO. When a solution of 10% trehalose and 90% TOAC in DMF is evaporated to dryness, a glass with a frosted or opalescent appearance results. Under the microscope, this is seen to be a very uniform distribution of spherical glassy microbeads of uniform size in a continuous matrix (FIGS. 16 and 17). By rough measurement with an eyepiece graticule, the size of the microbeads is about 4 micrometers in diameter.

Figure 18:
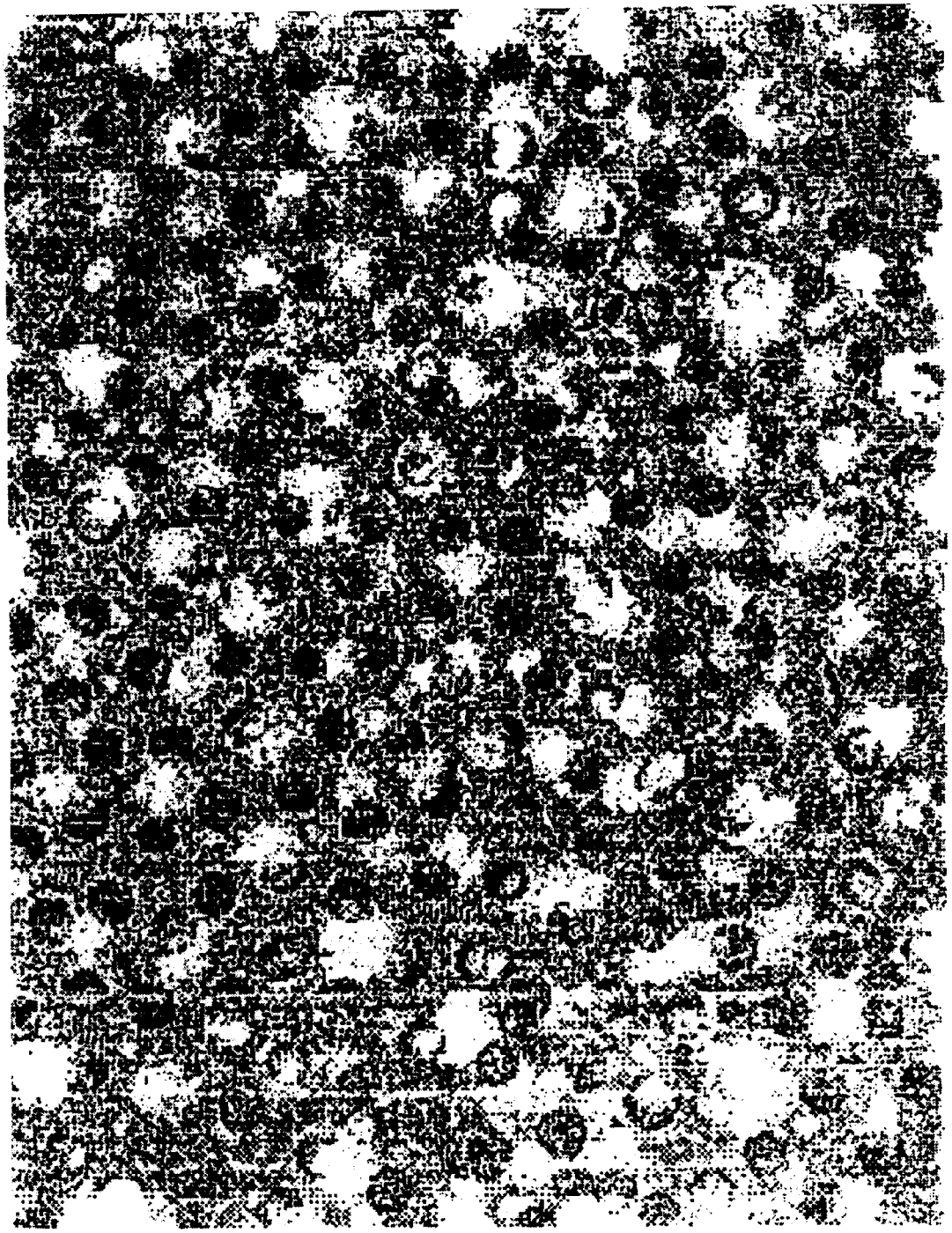
FIG. 18 is a photomicrograph of a coformulation glass comprising 10% trehalose in TOAC with methyl green and Oil red O dried from DMF.

The identity of the 2 phases was verified by incorporating a small quantity of the intensely hydrophobic lipid dye, Oil Red O together with a small quantity of the hydrophilic dye, Methylene Green in the solution in DMF before making the glass. As expected, the hydrophobic Oil Red O partitioned exclusively into the continuous phase, revealing it to be TOAC, whereas the hydrophilic Methylene Green partitioned exclusively into the discontinuous uniform particles revealing them to be trehalose (FIG. 18). The composite glass thus formed consisted of a very uniform and stable glass in glass "solid emulsion" or "solid suspension" rather than solid solutions such as are seen with the hydrophobic guest substances XPDO, CSA or Oil Red O.

When the same mixtures of trehalose and TOAC is evaporated from solution in DMSO, the appearance of the composite glass is different. In this case, the glass is more transparent and under the microscope the discontinuous trehalose phase is in 2 forms. One form is a very fine dispersion of extremely small trehalose particles uniformly dispersed throughout the continuous matrix. The other form consists of larger spherical beads of trehalose concentrated in a cluster in the center of the composite glass.

Without wishing to be bound by any one theory, it seems likely that the different patterns found reflect differences in the solubility of the two carbohydrates in the solvents used so that their deposit from solution occurred at different stages of the evaporation of the solvent. Suggestive evidence in confirmation of this explanation was found in experiments to produce composite glasses in the opposite orientation i.e. with a hydrophobic guest substance dispersed finely in a hydrophilic continuous matrix.

g) Toxicity of HDC Glasses

A saturated solution of TOAC in deionised distilled water (0.42 g in 20 mls) was tested for toxicity in vitro using the African Green monkey kidney-derived cell line Vero, in either a 10-fold serial dilution or by adding the TOAC powder directly to the tissue culture medium. No toxic effects were observed in the week of culture and cell division was normal.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

What is claimed is:

1. A composition comprising a solid dose delivery system comprising a vehicle and an effective amount of at least one guest substance wherein the vehicle comprises a hydrophobic derivatized carbohydrate (HDC).

2. The composition according to claim 1, further comprising at least one physiologically acceptable glass selected from the group consisting of carboxylate, nitrate, sulfate, and bisulfate.

3. The composition according to claim 1, wherein the HDC has a carbohydrate backbone and more than one hydroxyl group substituted with a less hydrophilic derivative thereof.

4. The composition according to claim 3, wherein the derivative is an ester or ether of any carbon chain length or type or any functional modifications thereof, wherein the functional modifications are selected from the group consisting of replacing the oxygen atom by a heteroatom.

5. The composition according to claim 4, wherein the HDC is selected from the group consisting of sorbitol hexaacetate, α-Glucose pentaacetate, β-Glucose pentaacetate, 1-0-Octyl-β-D-Glucose tetraacetate, trehalose octaacetate, trehalose octapropanoate, sucrose octaacetate, sucrose octapropanoate, cellobiose octaacetate, cellobiose octapropanoate, raffinose undecaacetate and raffinose undecapropanoate.

6. The composition according to claim 1, wherein the guest substance has increased stability in the presence of elevated temperatures or organic solvents.

7. The composition according to claim 1, wherein the form of the solid dose is selected from the group consisting of lozenge, tablet, disc, film, suppository, needle, microneedle, microfibers, particle, microparticle, sphere, microspheres, powders, and implantable devices.

8. The composition according to claim 7, wherein the particle is in the form of a needle of the dimensions 1–50 microns in diameter and 5–150 microns in length.

9. The composition according to claim 7, wherein the particle is in the form of a needle of the dimensions 0.1–4 mm in diameter and 1–30 mm in length.

10. The composition according to claim 1, wherein the guest substance is selected from the group consisting of pharmaceutical agents and biological modifiers.

11. The composition according to claim 10, wherein the guest substance is a pharmaceutical agent selected from the group consisting of antlinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs and, opioids.

12. The composition according to claim 1, wherein the guest substance is an organic selected from the group consisting of pharmaceutically active chemicals.

13. The composition according to claim 1, wherein the guest substance is a hormone selected from the group consisting of peptide, steroid and corticosteroid.

14. The composition according to claim 13, wherein the hormone is steroid and is selected from the group consisting of estrogen, progesterone, testosterone and physiologically active analogs thereof.

15. The composition of claim 1, wherein the vehicle comprises a hydrophobic derivatized carbohydrate (HDC) in which the guest substance can be dried and stored.

16. The composition of claim 1, wherein the vehicle comprises a hydrophobic derivatized carbohydrate (HDC) in which the guest substance can be dried and stored without losses in activity.

17. The composition of claim 1, wherein the hydrophobic derivatized carbohydrate (HDC) is non-toxic.

18. The composition of claim 1, wherein the vehicle comprises a hydrophobic derivatized carbohydrate (HDC) which is glassy or amorphous.

19. The composition of claim 1, wherein composition is capable of controlled release of the guest substance.

20. The composition of claim 1, wherein the composition is resistant to devitrification.

21. The composition of claim 1, wherein the HDC is a carbohydrate no greater than a pentasaccharide, and wherein more than one hydroxyl group of the HDC is derivatized as an ester or ether.

22. The composition of claim 1, further comprising a stabilizing polyol.

23. The composition according to claim 22, further comprising at least one physiologically acceptable glass selected from the group consisting of carboxylate, nitrate, sulfate, and bisulfate.

24. The composition according to claim 22, wherein the HDC has a carbohydrate backbone and more than one hydroxyl group substituted with a less hydrophilic derivative thereof.

25. The composition according to claim 24, wherein the derivative is an ester or ether of any carbon chain length or type or any functional modifications thereof, wherein the functional modifications are selected from the group consisting of replacing the oxygen atom by a heteroatom.

26. The composition according to claim 25, wherein the HDC is selected from the group consisting of sorbitol hexaacetate, α-Glucose pentaacetate, β-Glucose pentaacetate, 1-0-Octyl-β-D-Glucose tetraacetate, trehalose octaacetate, trehalose octapropanoate, sucrose octaacetate, sucrose octapropanoate, cellobiose octaacetate, cellobiose octapropanoate, raffinose undecaacetate and raffinose undecapropanoate.

27. The composition according to claim 22, wherein the guest substance has increased stability in the presence of elevated temperatures or organic solvents.

28. The composition according to claim 22, wherein the form of the solid dose is selected from the group consisting of lozenge, tablet, disc, film, suppository, needle, microneedle, microfibers, particle, microparticle, sphere, microspheres, powders, and implantable devices.

29. The composition according to claim 28, wherein the particle is in the form of a needle of the dimensions 1–50 microns in diameter and 5–150 microns in length.

30. The composition according to claim 28, wherein the particle is in the form of a needle of the dimensions 0.1–4 mm in diameter and 1–30 mm in length.

31. The composition according to claim 22, wherein the guest substance is selected from the group consisting of pharmaceutical agents and biological modifiers.

32. The composition according to claim 31, wherein the guest substance is a pharmaceutical agent selected from the group consisting of antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs and, opioids.

33. The composition according to claim 22, wherein the guest substance is an organic selected from the group consisting of pharmaceutically active chemicals.

34. The composition according to claim 22, wherein the guest substance is a hormone selected from the group consisting of peptide, steroid and corticosteroid.

35. The composition according to claim 34, wherein the hormone is steroid and is selected from the group consisting of estrogen, progesterone, testosterone and physiologically active analogs thereof.

36. The composition of claim 22, wherein the vehicle comprises a hydrophobic derivatized carbohydrate (HDC) in which the guest substance can be dried and stored.

37. The composition of claim 22, wherein the vehicle comprises a hydrophobic derivatized carbohydrate (HDC) in which the guest substance can be dried and stored without losses in activity.

38. The composition of claim 22, wherein the hydrophobic derivatized carbohydrate (HDC) is non-toxic.

39. The composition of claim 22, wherein the vehicle comprises a hydrophobic derivatized carbohydrate (HDC) which is glassy or amorphous.

40. The composition of claim 22, wherein composition is capable of controlled release of the guest substance.

41. The composition of claim 22, wherein the composition is resistant to devitrification.

42. The composition of claim 22, wherein the HDC is a carbohydrate no greater than a pentasaccharide, and wherein more than one hydroxyl group of the HDC is derivatized as an ester or ether.

43. The composition of claim 22, wherein the vehicle comprises microspheres of the stabilizing polyol suspended within the HDC.

44. The composition of claim 22, wherein the vehicle comprises microspheres of the HDC suspended in the stabilizing polyol.

45. The composition of claim 22, wherein the vehicle comprises the stabilizing polyol coated with the HDC.

46. The composition of claim 1, wherein the guest substance is an immunosuppressive agent that is a peptide.

47. The composition of claim 46, wherein the guest substance is cyclosporine.

\* \* \* \* \*